US007635479B2

(12) United States Patent
Paterson et al.

(10) Patent No.: US 7,635,479 B2
(45) Date of Patent: *Dec. 22, 2009

(54) COMPOSITION AND METHODS FOR ENHANCING IMMUNOGENECITY OF ANTIGENS

(75) Inventors: Yvonne Paterson, Philadelphia, PA (US); George Raymond Gunn, III, Collegeville, PA (US); Christian Peters, Radnor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 964 days.

This patent is subject to a terminal disclaimer.

(21) Appl. No.: 10/239,703

(22) PCT Filed: Mar. 26, 2001

(86) PCT No.: PCT/US01/09736

§ 371 (c)(1),
(2), (4) Date: Aug. 7, 2003

(87) PCT Pub. No.: WO01/72329

PCT Pub. Date: Oct. 4, 2001

(65) Prior Publication Data

US 2007/0003567 A1    Jan. 4, 2007

(51) Int. Cl.
*A61K 39/02* (2006.01)
*A61K 39/09* (2006.01)
*A61K 38/17* (2006.01)
(52) U.S. Cl. .............. 424/185.1; 424/191.1; 424/192.1
(58) Field of Classification Search .............. 424/185.1, 424/190.1, 192.1; 530/350
See application file for complete search history.

(56) References Cited

U.S. PATENT DOCUMENTS

| 4,521,382 | A |   | 6/1985 | Kessick |
| 4,567,041 | A |   | 1/1986 | Likhite |
| 4,777,239 | A |   | 10/1988 | Schoolnik et al. |
| 4,816,253 | A |   | 3/1989 | Likhite et al. |
| 4,879,213 | A |   | 11/1989 | Fox et al. |
| 5,262,177 | A |   | 11/1993 | Brown et al. |
| 5,342,774 | A |   | 8/1994 | Boon et al. |
| 5,369,008 | A |   | 11/1994 | Arilnghause et al. |
| 5,643,599 | A | * | 7/1997 | Lee et al. ............... 424/450 |
| 5,681,570 | A |   | 10/1997 | Yang et al. |
| 5,824,538 | A |   | 10/1998 | Branstrom et al. |
| 5,830,702 | A |   | 11/1998 | Portnoy et al. |
| 5,858,682 | A |   | 1/1999 | Gruenwald et al. |
| 5,876,735 | A |   | 3/1999 | Reed |
| 5,877,159 | A |   | 3/1999 | Powell et al. |
| 6,015,567 | A |   | 1/2000 | Hudziak et al. |
| 6,051,237 | A | * | 4/2000 | Paterson ............... 424/200.1 |
| 6,306,404 | B1 |   | 10/2001 | LaPosta et al. |
| 6,333,169 | B1 |   | 12/2001 | Hudziak et al. |
| 6,479,258 | B1 |   | 11/2002 | Short |
| 6,521,449 | B1 |   | 2/2003 | Polack et al. |
| 6,565,852 | B1 |   | 5/2003 | Paterson |
| 6,767,542 | B2 |   | 7/2004 | Paterson et al. |
| 6,855,320 | B2 | * | 2/2005 | Paterson ............... 424/192.1 |
| 7,135,188 | B2 |   | 11/2006 | Paterson |
| 2003/0028206 | A1 |   | 2/2003 | Shiber |
| 2003/0202985 | A1 |   | 10/2003 | Paterson |
| 2003/0220239 | A1 |   | 11/2003 | Simard et al. |
| 2004/0228877 | A1 |   | 11/2004 | Dubensky et al. |
| 2005/0118184 | A1 |   | 6/2005 | Paterson et al. |
| 2005/0129715 | A1 |   | 6/2005 | Paterson et al. |
| 2006/0051380 | A1 |   | 3/2006 | Schulick et al. |
| 2006/0093582 | A1 |   | 5/2006 | Paterson et al. |
| 2006/0104991 | A1 |   | 5/2006 | Paterson et al. |
| 2006/0121053 | A1 |   | 6/2006 | Sweeney et al. |
| 2006/0205067 | A1 |   | 9/2006 | Paterson et al. |
| 2006/0210540 | A1 |   | 9/2006 | Paterson et al. |
| 2006/0233835 | A1 |   | 10/2006 | Paterson et al. |
| 2006/0269561 | A1 |   | 11/2006 | Paterson et al. |
| 2008/0124354 | A1 |   | 5/2008 | Paterson et al. |

FOREIGN PATENT DOCUMENTS

| EP | 0 902 086 | 3/1999 |
| JP | 01 178592 | 7/1989 |
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/10496 | 4/1999 |

(Continued)

OTHER PUBLICATIONS

Decatur et al, Science 290: 992-995, Nov. 2000.*
Paul et al, in Fundamental Immunology, Second edition Raven Press, p. 987-988, 1989.*
Boon et al, Ann. Rev. Immunol. 24: 175-208, 2006.*
An et al., "A recombinant minigene vaccine containing a nonameric cytotoxic-T-Lymphocyte epitope confers limited protection against *Listeria monocytogenes* infection." Infect. Immun., May 1996, vol. 64, No. 5, pp. 1685-1693.
Bielecki et al., "*Bacillus subtilis* expressing a haemolysin gene from *Listeria monocytogenes* can grow in mammalian cells", Nature 1990 354:175-176.

(Continued)

*Primary Examiner*—Phuong Huynh
(74) *Attorney, Agent, or Firm*—Mark S. Cohen; Pearl Cohen Zedek Latzer, LLP (57) ABSTRACT

Compositions and methods for enhancing the immunogenicity of an antigen via fusion to a non-hemolytic truncated form of listeriolysin or a PEST-like amino acid sequence derived from a prokaryotic organism are provided.

35 Claims, 3 Drawing Sheets

FOREIGN PATENT DOCUMENTS

| WO | WO 99/25376 | 5/1999 |
|---|---|---|
| WO | WO 01/27295 | 4/2001 |
| WO | WO 01/72329 | 10/2001 |
| WO | WO 03/015716 | 2/2003 |
| WO | WO 03/092600 | 11/2003 |
| WO | WO 2004/006837 | 1/2004 |
| WO | WO 2006/036550 | 4/2006 |
| WO | WO 2007/061848 | 5/2007 |
| WO | WO 2007/106476 | 9/2007 |
| WO | WO 2007/130455 | 11/2007 |

OTHER PUBLICATIONS

Decatur A.L. et al., "A PEST-Like Sequence in Listeriolysin O Essential for *Listeria monocytogenes* Pathogenicity", Science 2000 290:992-995.

Gentschev et al., "*Salmonella* Strain Secreting Active Listeriolysin Changes Its Intracellular Localization", Infect. Immun. 1995 63:4202-4205.

Ikonimidis et al., "Delivery of a Viral Antigen to the Class I Processing and Presentation Pathway by *Listeria monocytogenes*", J.Exp. Med. 1994 180:2209-2218.

Kaufman S.H. et al., "Impact of intracellular location of and antigen display by intracellular bacteria: implications for vaccine development", J. Immunol. Lett. 1999 65(1-2):81-84.

Kocks et al., "*L. monocytogenes*-induced actin assembly requires the actA gene product",. Cell., Feb. 1992, vol. 68, No. 3, pp. 521-531.

Lin et al., "Treatment of Established Tumors with a Novel Vaccine That Enhances Major Histocompatibility Class II Presentation of Tumor Antigen[1]", Cancer Res. 1996 56:21-26.

Mengaud et al., "Expression in *Escherichia coli* and sequence analysis of the listeriolysin O determinant of *Listeria monocytogenes*", Infect. Immun. Apr. 1988, vol. 56, No. 4, pp. 766-772.

Moriishi et al., Sequence analysis of the actA gene of *Listeria monocytogenes* isolated from human. Microbiol. Immunol. 1998, vol. 42, No. 2, pp. 129-132.

Pan et al., "Regression of Established Tumors in Mice Mediated by the Oral Administration of a Recombinant *Listeria monocytogenes* vaccine[1]", Cancer Res. 1995 55:4776-4779.

Realini et al., "Proposed roles in protein-protein association and presentation of peptides by MHC Class I receptors", FEBS Lett. 1994 348:109-113.

Rechsteiner and Rogers, "PEST sequences and regulation by proteolysis", TIBS 1996 21:267-271.

Sirard et al., "Intracytoplasmic delivery of Lidteriolysin O by a vaccinal strain of *Bacillus anthracis* induces CD8-mediated protection against *Listeria monocytogenes*." J Immunology. Nov. 1997, vol. 159, pp. 4435-4443.

Tanabe et al., "Induction of Protective T Cells against *Listeria monocytogenes* in Mice by Immunization with a Listeriolysin O-Negative Avirulent Strain of Bacteria and Liposome-Encapsulated Listeriolysin O", Infect. Immun. 1999 67(2):568-575.

Verma et al., "Delivery of class I and class II MHC-restricted T-cell epitopes of listeriolysin of *Listeria monocytogenes* by attenuated *Salmonella*", Vaccine. Feb. 1995, vol. 13, No. 2, pp. 142-150.

Wu et al., "Engineering an intracellular pathway for major histocompatibility complex class II presentation of antigens", Cancer Res. 1996 56:21-26.

An et al. (1996) "A recombinant minigene vaccine containing a nonameric cytoxic-T-Lymphocyte epitope confers limited protection against *Listeria monocytogenes* infection" *Infect. Immun* 64,(5):1685-1693.

Attwood, et al. (2000) "The Babel of Bioinformatics" *Science* 290(5491):471-473.

Bielecki et al. (1990) "*Bacillus subtilis* expressing a haemolysin gene from *Listeria monocytogenes* can grow in mammalian cells" *Nature* 354:175-176.

Boon, et al. (2006) "Human T cell responses against melanoma" *Annu Rev Immunol.* 24:175-208.

Bourquin, et al. (2000) "Myelin oligodendrocyte glycoprotein-DNA vaccination induces antibody-mediated autoaggression in experimental autoimmune encephalomyelitis" *Eur J Immunol* 30:3663-3671.

Darji, et al. (1997) "Oral somatic transgene vaccination using attenuated *S. typhimurium*" *Cell* 91:765-776.

Decatur, et al. (2000) "A PEST-like sequence in Listeriolysin O essential for *Listeria monocytogenes* pathogenicity" *Science* 290(5493):992-995.

Finn, et al. (2003) "Cancer vaccines: between the idea and the reality" *Nature Reviews Immunology* 3:630-641.

Gentschev et al. (1995) "*Salmonella* strain secreting active Listeriolysin changes its intracellular localization" *Infect. Immun.* 63:4202-4205.

Guzman, et al. (1998) "Attenuated *Listeria monocytogenes* carrier strains can deliver an HIV-1 gp120 T helper epitope to MHC class II-restricted human CD4+ T cells" *European Journal of Immunology* 28:1807-1814.

Ikonimidis, et al. (1994) "Delivery of a viral antigen to the class I processing and presentation oathway by *Listeria monocytogenes*" *Journal of Experimental Medicine* 180(6):2209-2218.

Jenson, et al. (1997) "Recombinant *Listeria monocytogenes* as a live vaccine vehicle and a probe for studying cell-mediated immunity" *Immunological Review* 158:147-157.

Kaufman, et al. (1999) "Impact of intracellular location of and antigen display by intracellular bacteria: implications for vaccine development" *J Immunol. Lett*, 65(1-2):81-84.

Kerksiek (1999) "T cell responses to bacterial infection" *Curr Opin. Immunol.* 1(4):400-405.

Kocks et al. (1992) "*L. monocytogenes*-induced actin assembly requires the actA gene product" *Cell* 68(3):521-531.

Lasa, et al. (1997) "Identification of two regions in the N-terminal domain of ActA involved in the actin comet tail formation by *Listeria monocytogenes*" *EMBO* 16(7):1531-40.

Lebrun, et al. (1996) "Internalin must be on the bacterial surface to mediate entry of *Listeria monocytogenes* into epithelial cells" *Molecular Microbiology* 21(3):579-592.

Lin, et al. (1996) "Treatment of established tumors with a novel vaccine that enhances Major Histocompatibility Class II presentation of tumor antigen" *Cancer Res.* 56:21-26.

Makela, et al. (1987) Hand Book of Experimental Immunology, vol. 1, chapter 3, pp. 3.1-3.13.

Mengaud, et al. (1988) "Expression in *Escherichia coli* and sequence analysis of the Listeriolysin O determinant of *Listeria Monocytogenes*" *Infection and Immunity* 56(4):766-772.

Mikayama, et al. (1993) "Molecular cloning and functional expression of a cDNA encoding gycosylation-inhibiting factor" *Proc. Natl. Acad. Sci. USA* 90:10056-10060.

Moriishi et al. (1998) "Sequence analysis of the actA gene of *Listeria monocytogenes* isolated from human" *Microbiol. Immunol.* 42(2):129-132.

Ngo, et al. (1994) The Protein Folding Problem and Tertiary Structure Prediction 492-495.

Paglia, et al. (1997) "The defined attenuated *Listeria monocytogenes* delta mp12 mutant is an effective oral vaccine carrier to trigger a long-lasting immune response against a mouse fibrosarcoma" *Eur J Immunol* 27:1570-1575.

Pan, et al. (1995) "Regression of established tumors in mice mediated by the oral administration of a recombinant *Listeria monocytogenes* vaccine" *Cancer Research* 55:4776-4779.

Paul, et al. (1989) "Fundamental Immunology", Second Edition, Raven Press, 987-988.

Realini et al. (1994) "Proposed roles in protein-protein association and presentation of peptides by MHC class I receptors" *FEBS Letters* 348:109-113.

Rechsteiner, et al. (1996) "PEST sequences and regulation by proteolysis" *TIBS* 21:267-271.

Safley, et al. (1991) "Role of Listeriolysin-o (LLO) in the T Lymphocyte response to infection with *Listeria monocytogenes*" *J Immunol.* 146(10):3604-3616.

Shen, et al. .(1998) "*Listeria monocytogenes* as a probe to study cell-mediated immunity" *Curr. Opin. Immunol.* 10(4):450-458.

Shen, H. et al. (1995) "Recombinant *Listeria monocytogenes* as a Live Vaccine Vehicle for the Induction of Protective Anti-Viral Cell-Mediated Immunity" *Proc. Natl. Acad Sci. USA* 92:3987-3991.

Sirard, et al. (1997) "Intracytoplasmic delivery of Listeriolysin O by a vaccinal strain of *Bacillus anthracis* induces CD8-mediated protection against *Listeria monocytogenes*" *J Immun.* 159:4435-4443.

Skoble, J. et al. (2000). "Three regions within acta promote arp2/3 complex-mediated actin nucleation and *Listeria monocytogenes* motility" *The Journal of Cell Biology* 150(3):527-537.

Skolnick, et al. (2000) "From genes to protein structure and function: novel applications of computational approached in the genomic era" *Trends in Biotech.* 18(1):34-39.

Smith, G.A. et al. (Sep. 1995). "Asymmetric Distribution of the *Listeria monocytogenes* ActA Protein is Required and Sufficient to Direct Actin-Based Motility" Molecular Microbiology 17:945-951.

Stryer, et al. (1998) Biochemistry, Third Edition, WH Freeman Company, New York, 31-33.

Tanabe et al. (1999) "Induction of Protective T Cells against *Listeria monocytogenes* in Mice by Immunization with a Listeriolysin O-Negative Avirulent Strain of Bacteria and Liposome-Encapsulated Listeriolysin O" *Infect. Immun.* 67(2):568-575.

Verma et al. (1995) "Delivery of class I and class II MHC-restricted T-cell epitopes of listeriolysin of *Listeria monocytogenes* by attenuated *Salmonella*", *Vaccine* 13(2):142-150.

Weiskirch, et al. (1997) "*Listeria monocytogenes*: a potent vaccine vector for neoplastic and infectious disease" *Immunol. Rev* 158:159-169.

Welch, M.D. et al. (1998) "Interaction of Human Arp2/3 Complex and the *Listeria monocytogenes* ActA Protein in Actin Filament Nucleation" *Science* 281:105-108.

Wu et al. (1996) "Engineering an intracellular pathway for major histocompatibility complex class II presentation of antigens" *Cancer Res.* 56:21-26.

Adams et al. (1992) "Cre-*lox* recombination in *Escherichia coli* cells. Mechanistic differences from the in vitro reaction." *J. Mol. Biol.* 226:661-673.

Allison et al. (1997) "Cloning and characterization of a *Prevotella melaninogenica* hemolysin." *Infect Immun.* 65(7):2765-71.

Anderson (1998) "Human gene therapy." *Nature.* Apr. 30;392(6679 Suppl):25-30.

Angelakopoulos et al. (2002) "Safety and shedding of an attenuated strain of *Listeria monocytogenes* with a deletion of actA/plcB in adult volunteers: a dose escalation study of oral inoculation." *Infect Immun.* 70(7):3592-601.

Awwad (1989) "Cyclophosphamide-induced immunologically mediated regression of a cyclophosphamide-resistant murine tumor: a consequence of eliminating precursor L3T4+ suppressor T-cells" *Cancer Res.* 49(7): 1649-1654.

Barry et al. (1992) "Pathogenicity and immunogenicity of *Listeria monocytogenes* small-plaque mutants defective for intracellular growth and cell-to-cell spread." *Infection and Immunity* 60 (4): 1625-32.

Bast et al. (1975) "Antitumor activity of bacterial infection. II. effect of *Listeria monocytogenes* on growth of a guinea pig hepatoma." *J Natl. Cancer Inst.*, 54(3): 757-761.

Bear (1986) "Tumor-specific suppressor T-cells which inhibit the in vitro generation of cytolytic T-cells from immune and early tumor-bearing host spleens." *Cancer Res.* April;46(4 Pt 1):1805-12.

Beatly, Dissertation Abstracts International, 2000, 61/10B:5224 Abstract Only.

Bernhard et al. (2002) "Vaccination against the HER-2/neu oncogenic protein." *Endocrine-Related Cancer*, 9:33-44.

Billington et al. (1997) "The *Arcanobacterium (Actinomyces) pyogenes* hemolysin, pyolysin, is a novel member of the thiol-activated cytolysin family." *J Bacteriol.* October;179(19):6100-6.

Bodmer et al. (1988) "Enhanced recognition of a modified peptide antigen by cytotoxic T cells specific for influenza nucleoprotein." *Cell* 52: 253-258.

Boyer et al. (2005) "DNA prime *Listeria* boost induces a cellular immune response to SIV antigens in the rhesus macaque model that is capable of limited suppression of SIV239 viral replication." *Virology.* Mar. 1;333(1):88-101.

Brasseur et al. (1992) "Human gene MAGE-1, which codes for a tumor-rejection antigen, is expressed by some breast tumors." *Int. J Cancer* 52(5):839-841.

Brockstedt et al. (2004) "*Listeria*-based cancer vaccines that segregate immunogenicity from toxicity." *Proc Natl Acad Sci USA.* 101(38):13832-7.

Bron et al. (2004) "Identification of *Lactobacillus plantarum* genes that are induced in the gastrointestinal tract of mice." *J Bacteriol.* September;186(17):5721-9.

Brown et al. (1988) "Site-specific integration in *Saccharopolyspora erythraea* and multisite integration in *Streptomyces lividans* of actinomycete plasmid pSE101." *J. Bacteriology* 170: 2287-2295.

Bruhn et al. (2005) "Characterization of anti-self CD8 T-cell responses stimulated by recombinant *Listeria monocytogenes* expressing the melanoma antigen TRP-2." *Vaccine.* Jul. 21;23(33):4263-72.

Brundage et al. (1993) "Expression and phosphorylation of the *Listeria monocytogenes* ActA protein in mammalian cells." *Proc. Natl. Acad. Sci. USA* 90: 11890-11894.

Bubert et al. (1997) "The *Listeria monocytogenes* iap gene as an indicator gene for the study of PrfA-dependent regulation." *Mol Gen Genet.* September;256(1):54-62.

Burnham (2003) "Bad bugs: good for cancer therapy?" *Drug Discovery Today* 8(2):54-55.

Calendar et al. Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.

Camilli et al. (1993) "Dual roles of plcA in *Listeria monocytogenes* pathogenesis." *Mol. Microbiol.* 8:143-157.

Carbone (1989) "Induction of ovalbumin-specific cytotoxic T cells by in vivo peptide immunization." *J Exp Med* 169:603-612.

Carbone (1990) "Class I-restricted processing and presentation of exogenous cell-associated antigen in vivo." *J Exp Med* 171:377-387.

Chamberlain et al. (2000) "Innovations and strategies for the development of anticancer vaccines." *Expert Opinion on Pharmacotherapy* 1(4):603-614.

Courvalin et al. (1995) "Gene transfer from bacteria to mammalian cells." *C R Acad Sci III.* December;318(12):1207-12.

Cunto-Amesty et al. (2003) "Strategies in cancer vaccines development." *Int J Parasitol.* 33(5-6):597-613.

Dakappagari et al. (2000) "Prevention of mammary tumors with a chimeric HER-2 B-cell epitope peptide vaccine." *Cancer Res.* Jul. 15;60(14):3782-9.

Darji et al. (2003) "Induction of immune responses by attenuated isogenic mutant strains of *Listeria monocytogenes*." *Vaccine* 1;21 Suppl 2:S102-9.

Darji et al. (1995) "Hyperexpression of listeriolysin in the nonpathogenic species *Listeria innocua* and high yield purification." *J Biotechnol.* Dec. 15;43(3):205-12.

Darji et al. (1995) "Listeriolysin generates a route for the presentation of exogenous antigens by major histocompatibility complex class I." *Eur J Immunol.* October;25(10):2967-71.

Darji et al. (1997) "TAP-dependent major histocompatibility complex class I presentation of soluble proteins using listeriolysin." *Eur J Immunol.* June;27(6):1353-9.

Dermime et al. (2004) "Vaccine and antibody-directed T cell tumour immunotherapy." *Biochim Biophys Acta.* 1704(1):11-35.

Deshpande et al. (1997) "Isolation of a contact-dependent haemolysin from *Mycobacterium tuberculosis.*" *J Med Microbiol.* March;46(3):233-8.

Dietrich et al. (1998) "Delivery of antigen-encoding plasmid DNA into the cytosol of macrophages by attenuated suicide *Listeria monocytogenes*" *Nature Biotechnology* 15:181-185.

Dietrich et al. (2001) "From evil to good: a cytolysin in vaccine development." *Trends Microbiol.* January;9(1):23-8.

Dramsi et al. (1995) "Entry of *Listeria monocytogenes* into hepatocytes requires expression of inlB, a surface protein of the internalin multigene family." *Mol Microbiol.* 16(2):251-61.

Dunn et al. (1991) "Selective radiation resistance of immunologically induced T cells as the basis for irradiation-induced T-cell-mediated regression of immunogenic tumor." *J Leukoc Biol.* 49(4): 388-396.

Ebert et al. (1990) "Selective immunosuppressive action of a factor produced by colon cancer cells." *Cancer Res.* 50(19): 6158-6161.

Ezzel et al. (1995) J. NIH Res., vol. 7, p. 46.

Falk et al. (1991) "Identification of naturally processed viral nonapeptides allows their quantification in infected cells and suggests an allele-specific T cell epitope forecast" *J Exp Med.* 174(2):425-434.

Frankel et al. (1995) "Induction of cell-mediated immune responses to human immunodeficiency virus type 1 Gag protein by using *Listeria monocytogenes* as a live vaccine vector." *J. Immunol.* 155:4775-4782.

Frey (1993) "Rat adenocarcinoma 13762 expresses tumor rejection antigens but tumor-bearing animals exhibit tumor-specific immunosuppression." *Clin Immunol Immunopathol.* 69(2):223-233.

Friedman et al. (2000) "Induction of human immunodeficiency virus (HIV)-specific CD8 T-cell responses by *Listeria monocytogenes* and a hyperattenuated *Listeria* strain engineered to express HIV antigens." *J. Virology* 74 9987-9993.

Fu et al. (1990) "Expansion of immunoregulatory macrophages by granulocyte-macrophage colony-stimulating factor derived from a murine mammary tumor." *Cancer Res.* 50(2):227-234.

Fujii (1987) "Significance of suppressor macrophages for immunosurveillance of tumor-bearing mice." *J Natl Cancer Inst.* 78(3):509-517.

Furukawa (1993) "Nude mouse metastatic models of human stomach cancer constructed using orthotopic implantation of histologically intact tissue." *Cancer Res.* 53(5):1204-1208.

Galen et al. (2001) "Can a 'flawless' live vector vaccine strain be engineered?" *Trends Microbiol.* 9(8):372-6.

Gentschev et al. (1996) "Development of antigen-delivery systems, based on the *Escherichia coli* hemolysin secreatiohn pathway." *Gene* 179:133-140.

Gilmore et al. (1989) "A *Bacillus cereus* cytolytic determinant, cereolysin AB, which comprises the phospholipase C and sphingomyelinase genes: nucleotide sequence and genetic linkage." *J Bacteriol.* February;171(2):744-53.

Glomski et al. (2002) "The *Listeria monocytogenes* hemolysin has an acidic pH optimum to compartmentalize activity and prevent damage to infected host cells." *J Cell Biol.* Mar. 18;156(6):1029-38.

Goebel et al. (1993) "*Listeria monocytogenes*—a model system for studying the pathomechanisms of an intracellular microorganism." *Zbl. Bakt.* 278:334-347.

Goossens et al. (1992) "Induction of protective CD8+ T lymphocytes by an attenuated *Listeria monocytogenes* actA mutant." *Int Immunol.* December;4(12):1413-8.

Goossens et al. (1995) "Attenuated *Listeria monocytogenes* as a live vector for induction of CD8+ T cells in vivo: a study with the nucleoprotein of the lymphocytic choriomeningitis virus." *Int Immunol.* May;7(5):797-805.

Gregory et al. (1997) "Internalin B promotes the replication of *Listeria monocytogenes* in mouse hepatocytes". *Infect Immun.* 65(12):5137-41.

Gunn (2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." *J Immunol.* 167(11) 6471-6479.

Gunn et al. (2002) "Recombinant Intra-cellular Bacteria as Carriers for Tumor Antigens." In *Vaccine Delivery Strategies*, Chapter 14, Eds. Guido Dietrich and Werner Goebel, Horizon Scientific Press, UK.

Gunn, Dissertation Abstracts International, 2001, 62/5B:2244 Abstract Only.

Gunn et al. (2001) "Listeriolysin—a useful cytolysin." Trends Microbio1.9(4):161-162.

Harty et al. (1996) "Primary and secondary immune responses to *Listeria monocytogenes*." *Curr Opin Immunol.* 8:526-530.

Hassan et al. (2004) "Mesothelin: a new target for immunotherapy." *Clin Cancer Res.* 10(12 Pt 1):3937-42.

Hauf et al. (1997) "*Listeria monocytogenes* infection of P388D1 macrophages results in a biphasic NF-kappaB (RelA/p50) activation induced by lipoteichoic acid and bacterial phospholipases and mediated by IkappaBalpha and IkappaBbeta degradation." *Proc Natl Acad Sci U S A.* Aug. 19;94(17):9394-9.

Hess et al. (1995) "*Listeria monocytogenes* p60 supports host cell invasion by and in vivo survival of attenuated *Salmonella typhimurium*." *Infect Immun.* May;63(5):2047-53.

Hess et al. (1996) "*Salmonella typhimurium* aroA- infection in gene-targeted immunodeficient mice: major role of CD4+ TCR-alpha beta cells and IFN-gamma in bacterial clearance independent of intracellular location." *J Immunol.* May 1;156(9):3321-6.

Hess et al. (1996) "Superior efficacy of secreted over somatic antigen display in recombinant *Salmonella* vaccine induced protection against listeriosis" *Proc. Nat. Acad. Sci.* 93:1458-1463.

Hess et al. (1997) "Protection against murine listeriosis by an attenuated recombinant *Salmonella typhimurium* vaccine strain that secretes the naturally somatic antigen superoxide dismutase." *Infect Immun.* April;65(4):1286-92.

Hess et al. (1998) "*Mycobacterium bovis* bacilli Calmette-Guerin strains secreting listeriolysin of *Listeria monocytogenes*" *Proc. Natl. Acad. Sci.* 95:5299-5304.

Higgins et al. (1998) "Bacterial delivery of DNA evolves." *Nat Biotechnol.* February;16(2):138-9.

Hodgson (2000) "Generalized transduction of serotype 1/2 and serotype 4b strains of *Listeria monocytogenes*." *Mol Microbiol.* 35(2):312-23.

Hu et al. (2004) "*Escherichia coli* expressing recombinant antigen and listeriolysin O stimulate class I-restricted CD8+ T cells following uptake by human APC." *J. Immunology* 172:1595-1601.

Huang et al. (1994) "Role of bone marrow-derived cells in presenting MHC class I-restricted tumor antigens." *Science* 264961-965.

Hussain et al. (2004) "CD4+CD25+ regulatory T cells that secrete TGFbeta and IL-10 are preferentially induced by a vaccine vector." *J Immunother.* September-October;27(5):339-46.

Ikonomidis et al. (1994) Abstract E-90, Abstracts, 94th General Meeting of the American Society for Microbiology, May 23-27.

Jensen (1997) "Recombinant *Listeria monocytogenes* vaccination eliminates papillomavirus-induced tumors and prevents papilloma formation from viral DNA." *J Virol.* 71(11):8467-8474.

Jensen et al. (1997) "Recombinant *Listeria monocytogenes* as a live vaccine vehicle and a probe for studying cell-mediated immunity" *Immunological Review* 158:147-157.

Jones et al. (1994) "Characterization of *Listeria monocytogenes* pathogenesis in a strain expressing perfringolysin O in place of listeriolysin O." *Infect. Immun.* 62:5608-5613.

Kovacsovics-Bankowski et al. (1993) "Efficient major histocompatibility complex class I presentation of exogenous antigen upon phagocytosis by macrophages." *Proc. Natl. Acad. Sci. USA* 90:4942-4946.

Lamikanra et al. (2001) "Regression of established human papillomavirus type 16 (HPV-16) immortalized tumors in vivo by vaccinia viruses expressing different forms of HPV-16 E7 correlates with enhanced CD8(+) T-cell responses that home to the tumor site." *J. Virology* 75(20):9654-9664.

Lampson et al. (1993) "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ." *Cancer Research* 53:176-182.

Lara-Tejero et al. (2004) "T cell responses to *Listeria monocytogenes*." *Curr Opin Microbiol.* 7(1):45-50.

Lauer et al. (2002) "Construction, characterization, and use of two *Listeria monocytogenes* site-specific phage integration vectors." *J. Bacteriology* 184: 4177-4186.

Lauer et al. ASM Meeting, Abstract 1999.

Leão et al. (1995) "A species-specific nucleotide sequence of *Mycobacterium tuberculosis* encodes a protein that exhibits hemolytic activity when expressed in *Escherichia coli*." *Infect Immun.* November;63(11):4301-6.

Lee et al. (1991) "Construction of single-copy integration vectors for *Staphylococcus aureus*." *Gene* 103:101-5.

Lehner et al. (1996) "Processing and delivery of peptides presented by MHC class I molecules." *Curr Opin Immunol.* 8(1):59-67.

Lejeune (1994) "Nitric oxide involvement in tumor-induced immunosuppression." *J Immunol.* 152(10):5077-5083.

Liau et al. (2002) "Tumor immunity within the central nervous system stimulated by recombinant *Listeria monocytogenes* vaccination." *Cancer Res*. 62(8)2287-93.

Lin et al. (2002) "Oral vaccination with recombinant *Listeria monocytogenes* expressing human papillomavirus type 16 E7 can cause tumor growth in mice to regress." *Int J Cancer*. Dec. 20;102(6):629-37.

Lingnau et al. (1995) "Expression of the *Listeria monocytogenes* EGD inlA and inlB genes, whose products mediate bacterial entry into tissue culture cell lines, by PrfA-dependent and -independent mechanisms." *Infect Immun*. October;63(10):3896-903.

Loeffler et al. (2006) "Comparison of different live vaccine strategies in vivo for delivery of protein antigen or antigen-encoding DNA and mRNA by virulence-attenuated *Listeria monocytogenes*." *Infect Immun*. July;74(7):3946-57.

Loessner et al. (1995) "Heterogeneous endolysins in *Listeria monocytogenes* bacteriophages: a new class of enzymes and evidence for conserved holin genes within the siphoviral lysis cassettes." *Mol Microbiol*. June;16(6):1231-41.

Loessner et al. (2000) "Complete nucleotide sequence, molecular analysis and genome structure of bacteriophage A118 of *Listeria monocytogenes*: implications for phage evolution." *Molecular Microbiology* 35(2):324-40.

Mandal et al. (2002) "Listeriolysin O-liposome-mediated cytosolic delivery of macromolecule antigen in vivo: enhancement of antigen-specific cytotoxic T lymphocyte frequency, activity, and tumor protection." *BBA* 1563 7-17.

Manjili et al. (2003) "HSP110-HER2/neu chaperone complex vaccine induces protective immunity against spontaneous mammary tumors in HER-2/neu transgenic mice." *J Immunol*. Oct. 15;171(8):4054-61.

Marquis et al. (1997) "Proteolytic pathways of activation and degradation of a bacterial phospholipase C during intracellular infection by *Listeria monocytogenes*." *J. Cell Biol*. 137:1381-1392.

Martin et al. (1986) "Nucleotide sequence of the tetM tetracycline resistance determinant of the streptococcal conjugative shuttle transposon Tn1545." *Nucleic Acid Res*. 14:7047-7058.

Marx et al. (2002) "Broad-host-range cre-lox system for antibiotic marker recycling in gram-negative bacteria." *Biotechniques*. November;33(5):1062-7.

McLaughlan et al. (1998) "Molecular characterization of an autolytic amidase of *Listeria monocytogenes* EGD." *Microbiology*. May;144(Pt 5):1359-67.

Mlynárová et al. (2002) "The promiscuity of heterospecific lox sites increases dramatically in the presence of palindromic DNA." *Gene*. Aug. 21;296(1-2):129-37.

Mollet et al. (1993) "Directed genomic integration, gene replacement, and integrative gene expression in *Streptococcus thermophilus*." *J. Bacteriology* 175:4315-4324.

Ochsenbein et al. (1999) "A comparison of T cell memory against the same antigen induced by virus versus intracellular bacteria." *Proc Natl Acad Sci U S A*. Aug. 3;96(16):9293-8.

Oscarsson et al. (1996) "Induction of haemolytic activity in *Escherichia coli* by the slyA gene product." *Mol Microbiol*. April;20(1):191-9.

Palmeros et al. (2000) "A family of removable cassettes designed to obtain antibiotic-resistance-free genomic modifications of *Escherichia coli* and other bacteria." *Gene*. Apr. 18;247(1-2):255-64.

Pan (1999) "Regression of established B16F10 melanoma with a recombinant *Listeria monocytogenes* vaccine." *Cancer Res* 59(20):5264-5269.

Pan et al. (1995) "A recombinant *Listeria monocytogenes* vaccine expressing a model tumour antigen protects mice against lethal tumour cell challenge and causes regression of established tumours." *Nature Med*. 1:471-477.

Parida et al. (1998) "Internalin B is essential for adhesion and mediates the invasion of *Listeria monocytogenes* into human endothelial cells." *Mol Microbiol*. April;28(1):81-93.

Peng et al. (2004) "The ability of two *Listeria monocytogenes* vaccines targeting human papillomavirus-16 E7 to induce an antitumor response correlates with myeloid dendritic cell function." *J. Immunol*. 172:6030-6038.

Penichet et al. (2001) "Antibody-cytokine fusion proteins for the therapy of cancer." *J. Immunological Methods* 248:91-101.

Peters et al. (2003) "Tailoring host immune responses to *Listeria* by manipulation of virulence genes—the interface between innate and acquired immunity." *FEMS Immunol Med Microbiol*. Apr. 1;35(3):243-53.

Pfeifer et al. (1993) "Phagocytic processing of bacterial antigens for class I MHC presentation to T cells." *Nature*. Jan. 28;361(6410):359-62.

Pupa et al. (2001) "Prevention of spontaneous neu-expressing mammary tumor development in mice transgenic for rat proto-neu by DNA vaccination." *Gene Ther*. January;8(1):75-9.

Quénée et al. (2005) "Combined sacB-based negative selection and cre-lox antibiotic marker recycling for efficient gene deletion in *Pseudomonas aeruginosa*." *Biotechniques*. January;38(1):63-7.

Radford et al. (2002) "A recombinant *E. coli* vaccine to promote MHC class I-dependent antigen presentation: application to cancer immunotherapy." *Gene Therapy* 9:1455-1463.

Radford et al. (2003) "Recombinant *E. coli* efficiently delivers antigen and maturation signals to human dendritic cells: presentation of MART1 to CD8+ T cells." *Int. J. Cancer* 105:811-819.

Raveneau et al. (1992) "Reduced virulence of a *Listeria monocytogenes* phospholipase-deficient mutant obtained by transposon insertion into the zinc metalloprotease gene." *Infect. Immun*. 60: 916-921.

Reiter et al. (1989) "Transfer RNA genes frequently serve as integration sites for prokaryotic genetic elements." *Nucleic Acids Research* 17(5)1907-14.

Renard et al. (2003) "HER-2 DNA and protein vaccines containing potent Th cell epitopes induce distinct protective and therapeutic antitumor responses in HER-2 transgenic mice." *J Immunol*. 171(3):1588-95.

Repique (1992) "Immunosuppression derived from human B-lymphoblastoid and melanoma cell lines." *Cancer Invest*. 10(3):201-208.

Roden et al. (2004) "Vaccination to prevent and treat cervical cancer." *Hum Pathol* 35(8):971-82.

Rüssmann et al. (1998) "Delivery of epitopes by the *Salmonella* type III secretion system for vaccine development." *Science*. Jul. 24;281(5376):565-8.

Schafer et al. (1992) "Induction of a cellular immune response to a foreign antigen by a recombinant *Listeria monocytogenes* vaccine." *J. Immunol*. 149(1):53-59.

Scheirlinck et al. (1989) "Integration and expression of alpha-amylase and endoglucanase genes in the *Lactobacillus plantarum* chromosome." *Appl Environ Microbiol* 55(9):2130-7.

Schmidt et al. (1995) "Molecular Analysis of the Plasmid-Encoded Hemolysin of *Escherichia coli* O157:H7 Strain EDL 933" *Infection and Immunity*, 63(3):1055-1061.

Scortti et al. (2007) "The PrfA virulence regulon." *Microbes Infect*. August;9(10):1196-207.

Sewell et al. (2004) "Regression of HPV-positive tumors treated with a new *Listeria monocytogenes* vaccine." *Arch Otolaryngol Head Neck Surg* 130:92-97.

Sewell et al. (2004) "Recombinant *Listeria* vaccines containing PEST sequences are potent immune adjuvants for the tumor-associated antigen human papillomavirus-16 E7." *Cancer Res*. Dec. 15;64(24):8821-5.

Shen et al. (1998) "Compartmentalization of bacterial antigens: differential effects on priming of CD8 T cells and protective immunity." *Cell*. Feb. 20;92(4):535-45.

Shetron-Rama et al. (2002) "Intracellular induction of *Listeria monocytogenes* actA expression." *Infect. Immun*. 70:1087-1096.

Shimizu et al. (1994) "Effects of CD4+ and CD8+ T cells in tumor-bearing mice on antibody production." *Cancer Immunol Immunother*. 38(4):272-276.

Singh et al. (2005) "Fusion to Listeriolysin O and delivery by *Listeria monocytogenes* enhances the immunogenicity of HER-2/neu and reveals subdominant epitopes in the FVB/N mouse." *J Immunol*. Sep. 15;175(6):3663-73.

Slifka et al. (1996) "Antiviral cytotoxic T-cell memory by vaccination with recombinant *Listeria monocytogenes*." *J. Virol*. 70(5):2902-10.

Smith et al. (1995) "The two distinct phospholipases C of *Listeria monocytogenes* have overlapping roles in escape from a vacuole and cell-to-cell spread." *Infect. Immun.* 63 4231-4237.

Souders et al. (2006) "In vivo bactofection: *Listeria* can function as a DNA-cancer vaccine." *DNA Cell Biol.* March;25(3):142-51.

Stahl et al. (1984) "Replacement of the *Bacillus subtilis* subtilisin structural gene with an In vitro-derived deletion mutation." *J. Bacteriol* 158:411-418.

Starks et al. (2004) "*Listeria monocytogenes* as a vaccine vector: virulence attenuation or existing antivector immunity does not diminish therapeutic efficacy." *J. Immunology* 173:420-427.

Stitz et al. (1990) "Characterization and immunological properties of influenza A virus nucleoprotein (NP): cell-associated NP isolated from infected cells or viral NP expressed by vaccinia recombinant virus do not confer protection." *J Gen Virol.* 71(Pt 5):1169-1179.

Strugnell et al. (1990) "Stable expression of foreign antigens from the chromosome of *Salmonella typhimurium* vaccine strains." *Gene* 88:57-63.

Sun et al. (1990) "Isolation of *Listeria monocytogenes* small-plaque mutants defective for intracellular growth and cell-to-cell spread." *Infect. Immun.* 58 3770-3778.

Tilney et al. (1989) "Actin filaments and the growth, movement, and spread of the intracellular bacterial parasite, *Listeria monocytogenes.*" *J Cell Biol.* October;109(4 Pt 1):1597-608.

Vasil et al. (1982) "Cloning of a phosphate-regulated hemolysin gene (phospholipase C) from *Pseudomonas aeruginosa.*" *J Bacteriol.* October;152(1):431-40.

Vazquez-Boland et al. (1992) "Nucleotide sequence of the lecithinase operon of *Listeria monocytogenes* and possible role of lecithinase in cell-to-cell spread." *Infect. Immun.* 60:219-230.

Verch et al. (2004) "*Listeria monocytogenes*-based antibiotic resistance gene-free antigen delivery system applicable to other bacterial vectors and DNA vaccines." *Infect Immun.* November;72(11):6418-25.

Walker et al. (1994) "Tumor growth alters T cell and macrophage production of and responsiveness to granulocyte-macrophage colony-stimulating factor: partial dysregulation through interleukin-10." *Cell Immunol.* 154(1):342-357.

Watson et al. (1991) "Splenic macrophages from tumor-bearing mice co-expressing MAC-1 and MAC-2 antigens exert immunoregulatory functions via two distinct mechanisms." *J Leukoc Biol.* 49(2): 126-138.

Wei et al. (2005) "*Listeria monocytogenes* phosphatidylinositol-specific phospholipase C has evolved for virulence by greatly reduced activity on GPI anchors." *Proc. Natl. Acad. Sci. USA* 102: 12927-12931.

Weidt et al. (1994) "CD8+ T lymphocyte-mediated antiviral immunity in mice as a result of injection of recombinant viral proteins." *J Immunol.* Sep. 15;153(6):2554-61.

Wirth et al. (1986) "Highly efficient protoplast transformation system for *Streptococcus faecalis* and a new *Escherichia coli-S. faecalis* shuttle vector." *J Bacteriol.* 165(3):831-6.

Young et al. (1992) "Tumor-derived cytokines induce bone marrow suppressor cells that mediate immunosuppression through transforming growth factor beta." *Cancer Immunol Immunother.* 35(1): 14-18.

Young et al. (1995) "Holins: form and function in bacteriophage lysis." *FEMS Microbiol Rev.* August;17(1-2):191-205.

Zhang et al. (1993) "Functional replacement of the hemolysin A transport signal by a different primary sequence." *Proc Natl Acad Sci U S A.* May 1;90(9):4211-5.

Abachin et al., "Formation of D-alanyl-lipoteichoic acid is required for adhesion and virulence of *Listeria monocytogenes*", Molecular Microbiology, 2002, 43(1), 1-14.

Aggarwal et al., "Oral *Salmonella*: Malaria Circumsporozoite Recombinants Induce Specific CD8+ Cytotoxic T Cells", J. Exp. Med. 1990, 172, 1083-1090.

Alexander et al., "Characterization of an aromatic amino acid-dependent *Listeria monocytogenes* mutant: attenuation, persistance, and ability to induce protective immunity in mice", infection and immunity, May 1993, p. 2245-2248.

Amici et al., "DNA vaccination with full-length or truncated Neu induces protective immunity against the development of spontaneous mammary tumors in HER-2/neu transgenic mice", Gene Therapy, 2000, 7, 703-706.

Angelov et al., "Therapeutic vaccine for acute and chronic motor neuron diseases: Implications for amyotrophic lateral sclerosis", PNAS, Apr. 2003, vol. 100, No. 8, 4790-4795.

Anido et al., "Biosynthesis of tumorigenic HER2 C-terminal fragments by alternative initiation of translation", The EMBO Journal, 2006, 25, 3234-3244.

Bai et al., "Antigenic drift as a mechanism for tumor evasion of destruction by cytplytic T lymphocytes", J. Clin. Invest., 2003, 111, 1487-1496.

Bargmann et al., "The neu oncogene encodes an epidermal growth factor receptor-related protein", Nature, vol. 319, Jan. 1986, 226-230.

Baxeranis et al., Immunobiology of HER-2/neu oncoprotein and its potential application in cancer immunotherapy, Cancer Immunol. Immunother., 2004, 53, 166-175.

Beattie et al., "Cloning and characterization of T-cell-reactive protein antigens from *Listeria monocytogenes*", Infect. Immun., Sep. 1990; 58(9):2792-803.

Beatty, "A dual role for IFN-gamma in resolving the balance between tumor progression and regression", University of Pennsylvania, 2001, ii-xiii, 1-10.

Biragyn et al., "Models for Lymphoma", Current protocols in immunology, 2001, 20.6.1-20.6.30.

Boon et al., "Tumor Antigens Recognized by T Lymphocytes", Annu. Rev. Immunol. 1994,12, 337-365.

Bouwer et al., "Acquired immunity to an intracellular pathogen: immunologic recognition of *L. monocytogenes*-infected cells", Aug. 1997;158:137-46.

Bouwer et al., "Cytotoxic-T-lymphocyte responses to epitopes of listeriolysin O and p60 following infection with *Listeria monocytogenes*", Infect. Immun., Jul. 1996; 64(7):2515-22.

Bowie et al., "Deciphering the message in protein sequences: tolerance to amino acid substitutions" Science 247:1306-1310, 1990.

Bron et al., "Use of the alr gene as a food-grade selection marker in lactic acid bacteria", applied and environmental microbiology, Nov. 2002, vol. 68, No. 11, p. 5663-5670.

Bruder et al., "Efficient induction of cytotoxic CD8+ T cells against exogenous proteins: establishment and charcterization of a T cell line specific for the membrane protein ActA of *Listeria monocytogenes*", Eur. J. Immunol., Sep. 1998, 28(9):2630-9.

Brunner et al., "Quantitative assay of the lytic action of immune lymphoid cells on cr-labelled allogeneic target cells in vitro; inhibition by isoantibody and by drugs", Immunology, 1968, 14, 181-196.

Camilli et al., "*Listeria monocytogenes* mutants lacking phosphatidylinositol-specific phospholipase C are avirulent", J. Exp. Med., vol. 173, 751-754, Mar. 1991.

Catic et al., "Introduction of protein or DNA delivered via recombinant *Salmonella typhimurium* into the major histocompatibility complex class I pesentation pathway of macrophages", Microbes Infect., Feb. 1999, 1(2):113-21.

Chazin et al., "Transformation mediated by the human HER-2 gene independent of the epidermal growth factor receptor", Oncogene, 1992, 7, 1859-1866.

Cheever et al., "T-Cell Immunity to Oncogeneic Proteins Including Mutated RAS and Chimeric BCR-ABL", Ann. N.Y. Acad. Sci. 1993, 690:101-112.

Chen et al., "DNA Vaccines Encoding Full-Length or Truncated Neu Induce Protective Immunity against Neu-expressing Mammary Tumors", Cancer Research 58, 1965-1971, May 1, 1998.

Cho et al., "Structure of the extracellular region of HER2 alone and in complex with the herceptin Fab", Nature, vol. 421, Feb. 2003, 756-760.

Ciurea et al., "Viral presistence in vivo through selection of neutralizing antibody-escape variants", PNAS, Mar. 2000, vol. 97, No. 6, 2749-2754.

Cohen, J. "Cancer vaccines get a shot in the arm" Science 262:841-843.

Concetti et al., "Autoantibody to P185$^{erbB2/neu}$ oncoprotein by vaccination with xenogenic DNA", Cancer Immunol. Immunother., 1996, 43, 307-315.

Coussens et al., "Tyrosine kinase receptor with extensive homology to EGF receptor shares chromosomal location with neu oncogene", Sceince, vol. 230, 1132-1139, Dec. 1985.

Darji et al., "Antigen-specific T cell receptor antagonism by antigen-presenting cells treated with the hemolysin of *Lestria monocytogenes*: a novel type of immune escape", Eur. J. Immunol., Jul. 1997; 27(7):1696-703.

Darji et al., "T-cell anergy induced by antigen presenting cells treated with the hemolysin of *Listeria monocytogenes*", Immunol. Lett., Jun. 1997; 57(1-3):33-7.

Darji et al., "The role of the bacterial membrane protein ActA in immunity and protection against *Listeria monocytogenes*", J. Immunol., Sep. 1, 1998; 161(5):2414-20.

Di Carlo et al., "Inhibition of Mammary Carcinogenesis by systemic interleukin 12 or P185$^{neu}$ DNA vaccination in HER-2/neu transgenic BALB\c mice", Clinical Cancer Research, Mar. 2001, vol. 7, 830s-837s.

Disis et al., "Effect of dose on Immune Response in Patients vaccinated with an HER-2/neu Intracellular Domain Protein-Based vaccine", Journal of Clinical Oncology, vol. 22, No. 10, May 2004, 1916-1925.

Disis et al., "Generation of T-cell Immunity to the HER-2/neu Protein After Active Immunization with HER-2/neu Peptide-Based Vaccines", J. Clin. Oncol. 20:2624-2632, 2002.

Disis et al., "HER-2/neu protein: A target for antigen-specific immunotherapy of Human Cancer", Adv. Cancer Res 71: 373-371, 1997.

Disis et al., "Immunity to the HER-2/neu oncogenic protein", Ciba Found. Symp. 1994 187:198-211.

Disis et al., "Peptide-Based, but not whole protein, vaccines elicit immunity to HER-2/neu, an oncogenic self-protein", The Journal of Immunology, 1996, 156:3151-3158.

Doling et al., "Cytotoxic T-lymphocyte epitopes fused to anthrax toxin induce protective antiviral immunity", Infect. Immun., Jul. 1999, 67(7):3290-6.

Dumitrescu et al., "Understanding breast cancer risk—where do we stand in 2005?", J. Cell. Mol. Med., vol. 9, No. 1, 2005, pp. 208-221.

Dunn et al., "A critical function for type I interferons in cancer immunoediting", vol. 6, No. 7, Jul. 2005, Nature Immunology, 722-729.

Dunn et al., "Cancer immunoediting from immunosurveillance to tumor escape", Nature Immunology, vol. 3, No. 11, Nov. 2002, 991-998.

Dunn et al., "Interferon-γ and cancer Immunoediting", Immunologic Research, 2005, 32/1-3: 231-245.

Dunn, "The Immunobiology of cancer Immunosurveillance and Immunoediting", Immunity, Aug. 2004, vol. 21, 137-148.

Ercolini et al., "Recruitment of latent pools of high-avidity CD8+ T cells to the antitumor immune response", JEM, vol. 201, No. 10, May 2005, 1591-1602.

Esserman et al., "Vaccination with the extracellular domain of P185$^{neu}$ prevents mammary tumor development in neu transgenic mice", Cancer Immunol. Immunother., 1999, 47, 337-342.

Fields, "Preparation of antipeptide antibodies- Introduction to peptide synthesis", Current Protocols in Molecular Biology, 2002, 11.15.1-11.15.9.

Finn et al., "MUC-1 Epithelial Tumor Mucin-Based Immunity and Cancer Vaccines", Immuno. Rev. 1995, 145:61-89.

Foy et al., "Vaccination with HER-2/neu DNA or protein subunits protects against growth of HER-2/neu—expressing murine tumor", Vaccine, 19, 2001, 2598-2606.

Freshney, "Culture of animal cells- a manual of basic technique", Chapter 1, Second Edition, 1983, 1-6.

Gallo et al., "Xenogeneic immunization in mice using HER2 DNA delivered by an adenoviral vector", Int. J. Cancer, 113, 67-77, 2005.

Gansbacher et al., "Interleukin 2 Gene Transfer into Tumor Cells Abrogates Tumorigenicity and Induces Protective Immunity", J. Exp. Med. 1990, 172, 1217-1224.

Garay-Malpartida et al., "Caspredictor: a new computer-based tool for caspase substrate prediction", Bioinformatics, vol. 21, suppl. 1, 2005, p. 169-176.

Garcia-Lora et al., "MHC class I-deficient metastatic tumor variants immunoselected by T lymphocytes originate from the corrdinated downregulation of Apm components", Int. J. Cancer, 106, 521-527, 2003.

Gergory et al., 1997, "Internelin B promotes the replication of *Listeria monocytogenes* in mouse hepatocytes", Infect. Immun. 65(12):5137-41.

Gillespie et al., "The potential of melanoma antigen expression in cancer therapy", Cancer Treat. Rev. 1999, 25(4):219-27.

Glenting et al., "A plasmid selection system in *Lactococcus lactis* and its use for gene expression in *L lactis* and Ilumen kidney fibroblasts", Applied and environmental microbiology, Oct. 2002, vol. 68, No. 10, p. 5051-5056.

Golsteyn et al., "Structural and functional similarities between the human cytoskeletal protein zyxin and the ActA protein of *Listeria monocytogenes*." J. Cell Sci. 110:1893-1906, 1997.

Golumbek et al., "Treatment of Established Renal Cancer by Tumor Cells Engineered to Secrete Interleukin-4", Science 1991, 254, 713-716.

Gritzapis et al., "Vaccination with Human HER-2/neu (435-443) CTL peptide induces effective antitumor immunity against HER-2/neu -Expressing tumor cells in vivo", Cancer res., 66, 10, May 2006, 5452-5460.

Gunn, "Recombinant *Listeria monocytogenes* as a tumor therapeutic", University of Pennsylvania, 2001, ii-xiii, 1-10.

Guy et al., "Expression of the neu proto oncogene in the mammary epithelium of transgenic mice induces metastatic disease", Proc. Natl. Acad. Sci. USA, Nov. 1992, vol. 89, pp. 10578-10582.

Harris et al., "Molecular Basis for Hetrogeneity of the Human P53 protein", Molecular and Cellular Biology, Dec. 1986, vol. 6, No. 12, p. 4650-4656.

Harty et al., "CD8 T lymphocytes specific for the secreted p60 antigen protect against *Listeria monocytogenes* infection", J. Immunol., May 1, 1995; 154(9):4642-50.

Hess et al., "Live antigen carriers as tools for improved anti-tuberculosis vaccines", FEMS Immunol. Med. Microbiol., Feb. 1999, 23(2), 165-73.

Higgins et al., "Delivery of protein to the cytosol of macrophages using *Escherichia coli* K-12", Mol. Microbiol., Mar. 1999, 31(6):1631-41.

Hiltbold et al., "Mechanisms of processing and presentation of the antigens of *Listeria monocytogenes*", Infect. Agents Dis., Oct. 1993; 2(5):314-23.

Hiltbold et al., "The presentation of class I and class II epitopes of listeriolysin O is regulated by intracellular localization and by intrecellular localization and by intracellular localization and by intracellular spread of *Listeria monocytogenes*", Aug. 1996; 157(3):1163-75.

Hoogenboom et al., "By passing Immunisation—human antibodies from synthetic repertoires of germline V$_H$ gene segments rearranged in vitro", J. Mol. Biol., 1992, 227, 381-388.

Hueman et al., "Phase I clinical trial of a HER-2/neu peptide (E75) vaccine for the prevention of prostate—specific antigen recurrence in high-risk prostate cancer patients", Clin. Cancer Res., 11(20), Oct. 2005, 7470-7479.

Ikonomidis et al., "Influenza-specific immunity induced by recombinant *Listeria monocytogenes* vaccines", vaccine, vol. 15, No. 4, pp. 433-440, 1997.

Ikonomidis et al., ASM Las Vegas, the 94th general meeting of the american soceity for microbiology, May 23-27, 1994, Las Vegas convention center, Las Vages, Nevada, p. 29, 159, 662, 664.

Kawashima et al., "The Multi-epitope Approach for Immunotherapy for Cancer: Identification of Several CTL Epitopes from Various Tumor-Associated Antigens Expressed on Solid Epithelial Tumors", Hum. Immunol. 1998 59:1-14.

Khong et al., "Identification of multiple antigens recognized by tumor-infiltrating lymphocytes from a single patient: Tumor escape by antigen loss and loss of MHC expression", J. Immunother., 2004, 27, 184-190.

King et al., "Amplification of a Novel v-erbB-related gene in a human mammary carcinoma", Sceince, Sep. 1985, vol. 229, 974-976.

Kohler et al., "Expression of the iap gene coding for protein p60 of *Listeria monocytogenes* is controlled on the posttranscriptional level", Journal of Bacteriology, Aug. 1991, vol. 173, No. 15, p. 4668-4674.

Kruisbeek, "In vivo depletion of CD4- and CD8-specific T cells." Current Protocols in Immunology, John Wiley & Sons, Inc., eds., 1991, V.1, 4.1.1-4.1.2.

Kumar et al., "Amino acid variations at a single residue in an autoimmune peptide profoundly affect its properties: T-cell activation, major histocompatibility complex binding, and ability to block experimental allergic encephalomyelitis" PNAS, 87:1337-1341, 1990.

Kuntson et al., "neu Antigen Negative Variants can be generated after neu-specific antibody therapy in neu transgenic mice", Cancer Research 64, Feb. 2004, 1146-1151.

Kuntson et al., "Immunization with a HER-2/neu helper peptide vaccine generates HER-2/neu CD8 T-cell immunity in cancer patients." The Journal of Clinical Investigation, 107:477-484,2001.

Kyte et al., "A simple method for displaying the hydropathic character of a protein", J. Mol. Biol., 1982, 157, 105-132.

Lacey et al., "Phase IIa safety and immunogenicity of a therapeutic vaccine, TA-GW, in persons with genital warts", The Journal of Infectious Diseases, 1999, 179:612-8.

Lauer et al., "Systematic mutational analysis of the amino-terminal domain of the *Listeria monocytogenes* ActA protein reveals novel functions in actin-based motility." Molecular Microbiology 42(5):1163-1177, 2001.

Lee et al., "Delivery of macromolecules into cytosol using liposomes containing hemolysin from *Listeria monocytogenes*", J. Biol. Chem., Mar. 29, 1996; 271(13):7249-52.

Lee et al., "The murine MHC class I genes, H-2D and H-2L, and two genes reported to encode tumor-specific antigens", J. Exp. Med., Nov. 1988, vol. 168, 1719-1739.

Leitner et al., "DNA and RNA-based vaccines: prinicples, progress and prospects", Vaccine, Dec. 1999, 18(9-10):765-777.

Lipford et al., "Vaccination with immunodominant peptides encapsulated in Quil A-containing liposomes induces peptide-specific primary CD8+ cytotoxic T cells", Vaccine, Jan. 1994; 12(1):73-80.

Liu, "Vaccine developments", Nature medicine vaccine supplement, May 1998, vol. 4, No. 5, 515-519.

Marks et al., "By-Passing Immunization human antibodies from V-gene libraries displayed on phage", J. Mol. Biol. 1991, 222, 581-597.

Mata et al., "Evolution of a recombinant *Listeria monocytogenes* expressing an HIV protein that protects mice against viral challenge", Vaccine, 19, 2001, 1435-1445.

Mazzaccaro et al., "Major histocompatibility Class I presentation of soluble antigen facilitated by *Mycobacterium tuberculosis* infection", Proc. Natl. Acad. Sci. USA; Oct. 15, 1996; 93(21):11786-91.

McCarty et al., "Targeting p53 for Adoptive T-Cell Immunotherapy", Cancer Research 1998, 15:58 2601-5.

McKaig et al., "Human Papilloma virus and Head and Neck Cancer: Epidemiology and Molecular Biology", Head Neck 1998, 20 (3):250-65.

Miller et al., "Targeted vectors for gene therapy", the FASB Journal, Feb. 1995, vol. 9, p. 190-199.

Muller, "Expression of activated oncogenes in the murine mammary gland: transgenic models for human breast cancer", Cancer and Metastasis Reviews, 10:217-227, 1991.

Murali et al., "Structural analysis of P185$^{C-neu}$ and epidermal growth factor receptor tyrosine kinases: oligomerization of kinase domains", Proc. Natl. Acad. Sci. USA, vol. 93, pp. 6252-6257, Jun. 1996, Biochemistry.

Naz et al., "Novel human prostate-specific cDNA: molecular cloning, expression, and immunobiology of the recombinant protein", Biochemical and Biophysical Research Communications 297, 2002, 1075-1084.

Neeson et al., "A DNA prime-oral *Listeria* boost vaccine in rhesus macaques induces a SIV-specific CD8 T cell mucosal response characterized by high levels of α4β7 integrin and an effector memory phenotype", Virology, Oct. 2006, 354(2), 299-315.

Neeson et al., "Listeriolysin O is an improved protein carrier for lymphoma immunoglobulin idiotype and provides systemic protection against 38c/3 lymphoma", Cancer Immunol. Immunother., 2007, 13 pages.

Nielsen et al., "Peptide nucleic acids as therapeutic agents", Curr Opin Struct Biol 9(3): 353-357, Jun. 1997.

Pagano, J.S., "Epstein-Barr Virus: The First Human Tumor Virus and its Role in Cancer", Proc. Assoc. Am. Physicians 1999 111(6):573-80.

Pardoll, "Cancer Vaccines", Nature medicine vaccine supplement, May 1998, vol. 4, No. 5, 525-531.

"Paterson et al., Recombinant *Listeria monocytogenes* cancer vaccines", Curr Opinion Immunol 8(5): 664-669, Oct. 1996.

Paterson et al., Proceedings of the American Association for Cancer Research, Mar. 2000, 41:890, abstract # S25.

Paterson, "Rational approaches to immune regulation", Immunogenic Research, 27(2-3):451-462, Jun. 2003.

Piechocki et al., "Complementary Antitumor Immunity Induced by Plasmid DNA Encoding Secreted and Cytoplasmic Human ErbB-2", The Journal of Immunology, 2001, 167:3367-3374.

Pilgrim et al., "Bactofection of mammalian cells by *Listeria monocytogenes*: improvement and mechanism of DNA delivery", Gene Therapy, 2003, 10, 2036-2045.

Pilon et al., "Vaccination with Crytoplasmic ErbB-2 DNA Protects Mice from Mammary Tumor Growth Without Anti-ErbB-2 Antibody", The Journal of Immunology, 2001, 167:3201-3206.

Pricher et al., "Viral escape by selection of cytotoxic T cell-resistant virus variants in vivo" Nature, vol. 346, Aug. 1990, 629-633.

Pucci et al., "*Straphylococcus hameolyticus* contains two D-glutamic acid biosynthetic activities, a glutamate racemase and a D-amino acid transaminase", Journal of Bacteriology, Jan. 1995, vol. 177, No. 2, p. 336-342.

Punwaney et al., "Human Papillomavirus May be Common within Nasopharyngeal Carcinoma of Caucasian Americans: investigation of Epstein-Barr virus and human papillomavirus in Eastern and Western Nasopharyngeal Carcinoma using Ligation-Dependent polymerase chain reaction", Head Neck 1999 21(1):21-9.

Raffaghello et al., "Multiple defects of the antigen-processing machinery components in human neuroblastoma: immunotherapeutic implications", Oncogene, 2005, 24, 4634-4644.

Reilly et al., "HER-2/neu is a tumor rejection target in tolerized HER-2/neu transgenic mice", Cancer research 60, 3569-3576, Jul. 2000.

Restifo et al., "Identification of Human Cancers Deficient in Antigen Processing", J. Exp. Med. 1993, 177, 265-272.

Restifo et al., "The promise of nucleic acid vaccines", Gene Ther., Jan. 2000, 7(2): 89-92.

Rogers et al., "Amino acid sequences common to rapidly degraded proteins: the PEST hypothesis", Sceince, Reports, Oct. 1986, vol. 234, 364-368.

Romero et al., "Coordinated downregulation of the anti gen presentation machinery and HLA class I/β2-microglobulin complex is responsible for HLA-ABC loss in bladder cancer", Int. J. Cancer, 2005, 113, 605-610.

Rovero et al., "DNA Vacciniation Against Rat Her-2/Neu p185 More Effectively Inhibits Carcinogenesis Than Transplantable Carcinomas in Transgenic BaLB/c Mice", The Journal of Immunology, 2000, 165:5133-5142.

Scardino et al., "HER-2/neu and hTERT cryptic epitopes as Novel targets for broad spectrum tumor Immunotherapy", The Journal of Immunology, 2002, 168:5900-5906.

Schlom et al., "Cancer Vaccines:Moving Beyond Current Paradigms", Clin. Cancer Res. 2007; 13(13), Jul. 1, 2007.

Schneider et al., "Induction of pulmonary allergen-specific IgA responses or airway hyperresponsiveness in the absence of allergic lung disease following sensitization with limiting doses of ovalbumin-alum", Cellular Immunology, 212, 101-109, 2001.

Schnupf et al., "Phosphorylation, ubiquitination and degradation of listeriolysin O in mammalian cells: role of the PEST-like sequence." Cellular microbiology 8(2):353-364, 2006.

Schwartz, "T cell anergy", Annu. Rev. Immunol., 2003, 21, 305-34.

Scortti et al "The PrfA virulence regulon", Microbes and Infection xx, 2007, 1-12.

Seffernick et al., "Melamine deaminase and atrazine chlorohydrolase: 98 percent identical but functionally different." J. Bacteriol. 183(8):2405-10, Apr. 2001.

Serth et al., "Increased Levels of Human Papillomavirus Type 16 DNA in a Subset of Prostate Cancers", Cancer Res. 1999 15:59(4):823-5.

Shan et al., "Recombinant *Listeria monocytogenes* as a Live Vaccine Vehicle for the Induction of Protective Anti-Viral Cell-Mediated Immunity", Proc. Natl. Acad. Sci., USA, 92:3987-3991, Apr. 25, 1995.

Shrikant et al., "CTLA-4 blockade reverses CD8+ T cell tolerance to tumor by a CD4+ T cell- and IL-2-dependent mechanism", Immunity, Oct. 1999, vol. 11, 483-493.

Silverman et al., "Expression of c-myc, c-raf-1, and c-Ki-ras in azaserine-induced pancreatic carcinomas and growing pancreas in rats." Mol. Carcinog 3(6):379-86, 1990.

Singh et al., "Structure-Based Design of a Potent, Selective and Irreversible Inhibitor of the Catalytic Domain of the erbB receptor subfamily of protein tyrosine kinases", J. Med. Chem., 1997, 40, 1130-1135.

Singh et al., "Vaccination Strategy Determines the emergence and dominanace of CD8+ T-cell epitopes in a FVB/N Rat HER-2/neu mouse model of breast cancer", Cancer Res., 66, 15, Aug. 2006, 7748-7757.

Stover et al., "New Use of BCG for Recombinant Vaccines", Nature 1991, 351, 456-460.

Strych et al., "Mutant analysis shows that alanine racemases from *Pseudomonas aeruginosa* and *Escherichia coli* are dimeric", Journal of Bacteriology, Aug. 2002, p. 4321-4325.

Szalay et al., "Presentation of *Listeria monocytogenes* antigens by major histocompatibility complex class I molecules to CD8 cytotoxic T lymphocytes independent of listeriolysin secretion and virulence", Eur. J. Immunol., Jul. 1994; 24(7):1471-7.

Teitelbaum et al., "Mycobacterial infection of macrophages results in membrane-permeable phagosomes", Proc. Natl. Acad. Sci. USA, Dec. 21, 1999; 96(26):15190-5.

Thompson et al., "Pathogenicity and Immunogenicity of a *Listeria monocytogenes* strain that requires D-alanine for growth", Infection and Immunity, Aug. 1998, vol. 66, No. 8, p. 3552-3561.

Thull et al., "Recognition and management of hereditary breast cancer syndromes", The Oncologist, 2004; 9:13-24.

Townsend et al., "Tumor Rejection after Direct Costimulation of CD8+ T Cells by B7-Transfected Melanoma Cells", Science 1993, 259, 368-370.

Travis, "A Stimulating New Approach to Cancer Treatment", Science 1993, 259, 310-311.

Ulmanen et al., "Transcription and Translation of Foreign genes in *Bacillus subtilis* by the aid of a secretion vector", Journal of Bacteriology, Apr. 1985, vol. 162, No. 1, p. 176-182.

Uyttenhove et al., "Escape of mouse mastocytoma P815 after Nearly complete rejection is due to antigen-loss variants rather than immunosuppression", J. Exp. Med., vol. 157, Mar. 1983, 1040-1052.

Vazquez et al., "Diffrential regulation of Ia expression and antigen presentation by listeriolysin-producing versus non-producing strains of Listeria monocytogenes", J. Leukoc Biol., May 1996; 59(5):683-90.

Villanueva et al., "Listeriolysin is processed efficiently into an MHC class I-associated epitope in Listeria monocytogenes-infected cells", J. Immunol., Dec. 1, 1995; 155(11):5227-33.

Vines et al., "Identification and charcterization of nucleotide sequence difference in there virulence-associate genes of *Listeria monocytogenes* strains representing clinically important serotypes", Current Microbiology, May 1998, vol. 36, No. 5, pp. 309-318.

Vitiello et al., "Development of a Lipopeptide-based Therapeutic Vaccine to treat chronic HBV infection", J. Clin. Invest., vol. 95, Jan. 1995, 341-349.

Watson et al., "Immunosurveillance is active in colorectal cancer as downregulation but not complete loss of MHC class I expression correlates with a poor prognosis", Int. J. Cancer, 2006, 118, 6-10.

Wei et al., "Protection against mammary tumor growth by vaccination with full-length, modified human ErbB-2 DNA", Int. J. Cancer, 81, 748-754, 1999.

Wilson et al., "Transient expression of bacterial gene fragments in eukaryotic cells: implications for CD8(+) T cell epitope analysis", J. Immunol. Methods, Feb. 2000, 234(1-2):137-47.

Wingens et al., "Structural analysis of an epidermal growth factor / Transforming growth factor-α chimera with uniqe ErbB binding specificity", The Journal of Biological Chemistry, vol. 278, No. 40, Issue of Oct. 3, pp. 39114-39123, 2003.

Witkowski et al., "Conversion of a beta-ketoacyl synthase to a malonyl decarboxylase by replacement of the active-site cysteine with glutamine." Biochemistry 38(36):11643-50, Sep. 7, 1999.

Wunderlich et al., "Assays for T cell function: induction and measurement of cytotoxic T lymphocyte activity", Current Protocols in Immunology, 1997, vol. 3, p. 3.11.1-3.11.20.

Yaghmai et al., "Optimized regulation of gene expression using artificial transcription factors", Molecular Therapy, Jun. 2002, vol. 5, No. 6, 685-694.

Young et al., "Cloning and Expression of Influenza Virus Genes", The Origin of Pandemic Influenza Viruses, W.G. Laver, eds., Elsevier Science Publishing Co., Inc., NY, 1983, p. 129.

Zhang et al., "Selection of Tumor Antigens as Targets for Immune Attack Using Immunohistochemistry: Protein Antigens", Clin. Cancer Res. 1998 4:2669-2676.

Zubair et al., In: Vaccines for human Papillomavirus Infection and Anogential Disease (ed. Robert W. Tindle); 1999, pp. 173-192.

Zwickey et al., "Peptide epitopes from noncytosolic *Listeria monocytogenes* can be presented by major histocompatibiity complex class I molecules", Infect. Immun., May 1996; 64(5):1870-2.

Zwickey et al.,"Antigen secreted from noncytosolic *Listeria monocytogenes* is processed by the classical MHC class I processing pathway", J. Immunol., Jun. 1999, 162(11):6341-50.

Hausen et al., "Papillomaviruses causing cancer: evasion from host cell control in early events in carcinogenesis". J of the National Cancer Institute, 2000, vol. 92, pp. 690-698, abstract.

Jager et al., "Identification of NY-ESO-1 expressing epitopes presented by human histocompatibility antigen (HLA)-DRB* 0101-0103 and recognized by CD4+ T lymphocytes of patients with NY-ESO-1 expressing melanoma". J. Exp Med, 2000, vol. 191, pp. 625-630, abstract.

Maciag et al., "The first clinical use of a live-attenuated Listeria monocytogenes vaccine: a phase I safety study of Lm-LLOE7 in patients with advanced carcinoma of the cervix". Vaccine 27 (2009) 3975-3983.

Peng et al., "Adjuvant properties of listeriolysin O protein in a DNA vaccination strategy". Cancer Immunol Immunother, 2007, vol. 56, pp. 797-806, abstract.

Portnoy et al., "Molecular determinants of Listeria monocytogenes pathogenesis". Infection and Immunity, Apr. 1992, pp. 1263-1267.

* cited by examiner

SEQUENCE LISTING

```
<160> NUMBER OF SEQ ID NOS: 13

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
  1               5                  10                  15

Ser Pro Lys Thr Pro Ile Glu Lys Lys His Ala Asp Glu Ile Asp Lys
                 20                  25                  30

<210> SEQ ID NO 2
<211> LENGTH: 14
<212> TYPE: PRT
<213> ORGANISM: Listeria monocytogenes

<400> SEQUENCE: 2

Lys Thr Glu Glu Gln Pro Ser Glu Val Asn Thr Gly Pro Arg
  1               5                  10

<210> SEQ ID NO 3
<211> LENGTH: 28
<212> TYPE: PRT
<213> ORGANISM: Listeria monocytogenes

<400> SEQUENCE: 3

Lys Ala Ser Val Thr Asp Thr Ser Glu Gly Asp Leu Asp Ser Ser Met
  1               5                  10                  15

Gln Ser Ala Asp Glu Ser Thr Pro Gln Pro Leu Lys
                 20                  25
```

```
<210> SEQ ID NO 4
<211> LENGTH: 20
<212> TYPE: PRT
<213> ORGANISM: Listeria monocytogenes

<400> SEQUENCE: 4

Lys Asn Glu Glu Val Asn Ala Ser Asp Phe Pro Pro Pro Thr Asp
 1               5                  10                  15

Glu Glu Leu Arg
            20

<210> SEQ ID NO 5
<211> LENGTH: 33
<212> TYPE: PRT
<213> ORGANISM: Listeria monocytogenes

<400> SEQUENCE: 5

Arg Gly Gly Ile Pro Thr Ser Glu Glu Phe Ser Ser Leu Asn Ser Gly
 1               5                  10                  15

Asp Phe Thr Asp Asp Glu Asn Ser Glu Thr Thr Glu Glu Glu Ile Asp
            20                  25                  30

Arg

<210> SEQ ID NO 6
<211> LENGTH: 17
<212> TYPE: PRT
<213> ORGANISM: Streptococcus pyogenes

<400> SEQUENCE: 6

Lys Gln Asn Thr Ala Ser Thr Glu Thr Thr Thr Thr Asn Glu Gln Pro
 1               5                  10                  15

Lys

<210> SEQ ID NO 7
<211> LENGTH: 17
<212> TYPE: PRT
<213> ORGANISM: Streptococcus equisimilis

<400> SEQUENCE: 7

Lys Gln Asn Thr Ala Asn Thr Glu Thr Thr Thr Thr Asn Glu Gln Pro
 1               5                  10                  15

Lys

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: synthetic

<400> SEQUENCE: 8
gctagccctc ctttgattag tatattc                                           27

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 9
gcggatgaaa tcgataagca tggagataca cctaca                                 36
```

-continued

```
<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 10
cgcctacttt agctattcgt acctctatgt ggatgt                            36

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 11
gagtctttgg tattgggccc                                              20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 12
gctctagatt atggtttctg ag                                           22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 13
ggggtaccct cctttgatta gtatat                                       26
```

COMPOSITION AND METHODS FOR ENHANCING IMMUNOGENECITY OF ANTIGENS

INTRODUCTION

This invention was supported in part by funds from the U.S. government (NIH Grant No. CA69632) and the U.S. government may therefore have certain rights in the invention.

BACKGROUND OF THE INVENTION

Stimulation of an immune response is dependent upon the presence of antigens recognized as foreign by the host immune system. Bacterial antigens such as *Salmonella enterica* and *Mycobacterium bovis* BCG remain in the phagosome and stimulate CD4 T-cells via antigen presentation through major histocompatibility class II molecules. In contrast, bacterial antigens such as *Listeria monocytogenes* exit the phagosome into the cytoplasm. The phagolysosomal escape of *L. monocytogenes* is a unique mechanism which facilitates major histocompatibility class, I antigen presentation of listerial antigens. This escape is dependent upon the pore-forming sulfhydryl-activated cytolysin, listeriolysin O (LLO).

The ability of *L. monocytogenes* to break down the vacuole within a host cell and enter the cytoplasm has led to its use as a recombinant vaccine. U.S. Pat. No. 5,830,702 describes vaccines comprising attenuated mutants of *Listeria* spp. genetically engineered to express foreign antigens in the cytoplasm of infected macrophages and other cells. Several approaches for expressing the antigen in *Listeria* spp. are described including generation of a fusion protein of a selected foreign antigen and a listerial protein, preferably an enzyme involved in lysis of host vacuoles. In particular, a fusion protein encoding the hly promoter and the first 416 amino acids of LLO fused in-frame to the entire coding transformation to *Listeria monocytogenes* is demonstrated to secrete a 105 kDA protein that reacts with antiserum to LLO and NP (col. 24 of '702 patent). Recombinant *L. monocytogenes* secreting a fusion protein comprising listeriolysin O and NP (LLO-NP) was demonstrated to target infected cells for lysis by NP-specific class I-restricted cytotoxic T cells. In contrast, a hemolysin-negative *L. monocytogenes* strain expressing LLO-NP presented the antigen in a class II restricted manner (Ikonimidis et al. *J. Exp. Med.* 1994 180: 2209-2218). Thus, from these studies it was surmised that hemolysin-dependent bacterial escape from the vacuole is necessary for class I presentation in vitro.

The escape function of *L. monocytogenes* has also been transferred to *Bacillus subtilis* and attenuated *Salmonella* ssp. strains (Bielecki et al. *Nature* 1990 354:175-176, Gentschev et al. *Infect. Immun.* 1995 63:4202-4205). *S. enteric* and *M. bovis* BCG vaccine carriers which secrete listeriolysin O have also been constructed (Kaufman, S. H. and Hess, *J. Immunol. Lett.* January 1999 65(1-2):81-4). These constructs are taught to be capable of introducing antigens into the MHC class II and MHC class I pathway, resulting in stimulation of both CD4 and CD8 T-cells. Comparison of *S. enterica* vaccines which display the same listerial antigen in secreted and somatic form showed the secreted antigen display to be superior to the somatic antigen display (Kaufman, S. H. and Hess, *J. Immunol. Lett.* January 1999 65(1-2):81-4).

WO 99/10496 discloses recombinant BCG strains secreting hemolytically active hly with an improved MHC class I-restricted immune response for use as a vaccine against tuberculosis.

Administration of purified listeriolysin O encapsulated in liposomes has also been reported to be effective in the induction of antigen-specific Th1-dependent protective immunity to various kinds of intracellular parasitic bacteria in vivo (Tanabe et al. *Infect. Immun.* February 1999 67(2):568- in vivo (Tanabe et al. *Infect. Immun.* February 1999 67(2):568-75). PEST sequences in eukaryotic proteins have long been identified. It has been taught that proteins containing amino acid sequences that are rich in prolines (P), glutamic acids (E), serines (S) and threonines (T), generally, but not always, flanked by clusters containing several positively charged amino acids, have rapid intracellular half-lives (Rogers et al. Science 1986 234:364-369). Further, it has been shown that these sequences target the protein to the ubiquitin-proteosome pathway for degradation (Rechsteiner and Rogers TIBS 1996 21:267-271). This pathway is also used by eukaryotic cells to generate immunogenic peptides that bind to MHC class I and it has been hypothesized that PEST sequences are abundant among eukaryotic proteins that give rise to immunogenic peptides (Realini et al. FEBS Lett. 1994 348:109-113). Prokaryotic proteins do not normally contain PEST sequences because they do not have this enzymatic pathway.

However, a PEST-like sequence rich in the amino acids proline (P), glutamic acid (E), serine (S) and threonine (T) was recently identified at the amino terminus of LLO and demonstrated to be essential for *L. monocytogenes* pathogenicity (Decatur, A. L. and Portnoy, D. A. Science 2000 290: 992-995). Decatur and Portnoy teach that the presence of this PEST-like sequence in LLO targets the protein for destruction by proteolytic machinery of the host cell so that once the LLO has served its function and facilitated the escape of *L. monocytogenes* from the phagolysosomal vacuole, it is destroyed before it can damage the cells.

It has now been found that the immune response to an antigen can be enhanced by fusion of the antigen to a non-hemolytic truncated form of listeriolysin O (ΔLLO). It is believed that the observed enhanced cell mediated immunity and anti-tumor immunity of the fusion protein results from the

SUMMARY OF THE INVENTION

An object of the present invention is to provide a method for enhancing the immunogenicity of an antigen which comprises fusing to the antigen a non-hemolytic truncated form of listeriolysin O (ΔLLO). In a preferred embodiment, the antigen is fused to a PEST-like amino acid sequence derived from *L. monocytogenes*.

Another object of the present invention is to provide compositions with enhanced cell mediated immunity and anti-tumor immunity which comprise an antigen fused to a PEST-like amino acid sequence derived from a prokaryotic organism.

Yet another object of the present invention is to provide a method for invoking an enhanced cell mediated or anti-tumor immunogenic response to an antigen in an animal comprising administering to the animal a composition comprising an antigen fused to a PEST-like amino acid sequence derived from a prokaryotic organism.

DETAILED DESCRIPTION OF THE INVENTION

The present invention relates to a method for enhancing the immunogenicity of a selected antigen by fusion of the selected antigen to a non-hemolytic truncated form of listeriolysin O. It has now been found that fusion of an antigen to a non-hemolytic truncated form of listeriolysin O results in an antigen with enhanced immunogenicity as compared to antigen alone. This truncated form of listeriolysin O fused to an antigen better enables cell mediated immunity and anti-tumor immunity as compared to antigen alone. Further, these fusion proteins need not be expressed by *L. monocytogenes*, but rather can be expressed and isolated from other vectors and cell systems routinely used for protein expression and isolation.

Listeriolysin O (LLO) binds to cholesterol-containing membranes wherein it oligomerizes to form pores. The oligomerization is dependent on the presence of a reduced cystine residue at position 484 in the sequence that is required for oligomerization. The hly gene encodes a proprotein of 529 residues (GenBank Accession No. P13128), the first 25 amino acids are the signal sequence and are cleaved from LLO when it is secreted by the bacterium. Thus, the full length active LLO protein is approximately 504 residues. For purposes of the present invention, by "truncated form of LLO or ΔLLO" it is meant a fragment of LLO which does not contain the activation domain at the amino terminus including cystine 484. The present invention also relates to methods and compositions for enhancing cell mediated or anti-tumor immunity of a selected antigen by fusion of the selected antigen to a PEST-like amino acid sequence derived from a prokaryotic organism. For purposes of the present invention, by "PEST-like amino acid sequence" it is meant a peptide rich in the amino acids proline (P), glutamic acid (E), serine (S) and threonine (T). In a preferred embodiment the PEST-like amino acid sequence is derived from the amino acid terminus of Listeriolysin O (LLO), a hemolytic virulence factor of *L. monocytogenes*. In a more preferred embodiment, the PEST-like amino acid sequence comprises KENSISSMAPPASPPASPKTPIEKKHADEIDK (SEQ ID NO:1).

Enhanced cell mediated immunity was demonstrated for fusion proteins comprising an antigen and truncated LLO containing the PEST-like amino acid sequence, SEQ ID NO:1. The ΔLLO used in these experiments was 416 amino acids long as 88 residues from the amino terminus which is inclusive of the activation domain containing cystine 484 were truncated. However, it is believed that other ΔLLOs without the activation domain, and in particular cystine 484, will also be effective. More particularly, it is believed that fusion of an antigen to any ΔLLO including the PEST-like amino acid sequence, SEQ ID NO:1, can enhance cell mediated and anti-tumor immunity of the antigen.

Figure 1:
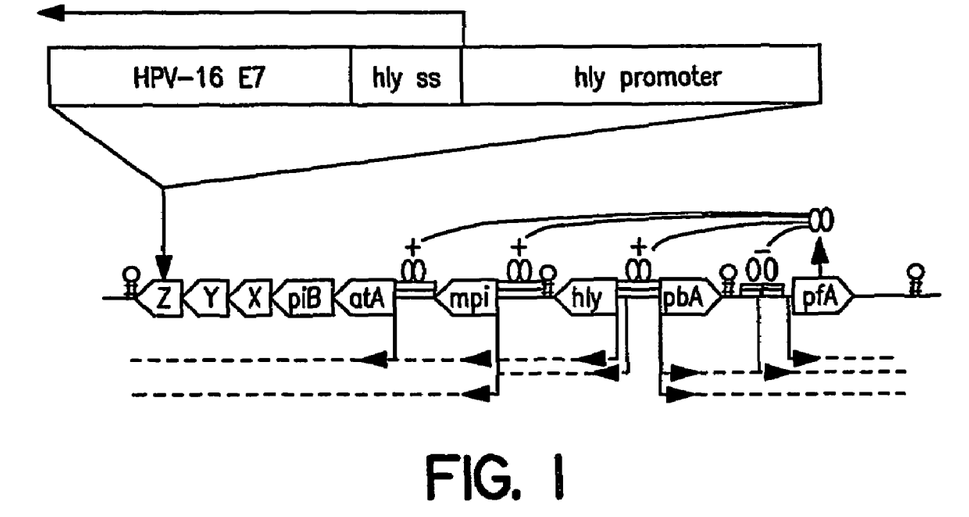
FIG. 1 is a diagram of an HPV-E7 chromosomal expression system constructed by integration of an E7 gene into the *Listeria* chromosome.

Enhanced immunogenicity of an antigen following fusion to a non-hemolytic truncated form of listeriolysin O was demonstrated. Specifically, experiments have been performed demonstrating that an *L. monocytogenes* vector that expresses and secretes a fusion product of Human *Papilloma* Virus (HPV) strain 16 E7 and listeriolysin, which comprises the PEST-like amino acid sequence SEQ ID NO:1, is a much more potent cancer immunotherapeutic for HPV immortalized tumors than a strain of *L. monocytogenes* that secretes the E7 protein alone. Experiments were also performed demonstrating that a recombinant *vaccinia* virus that carries the gene for the fusion protein LLO-E7 which contains the PEST-like amino acid sequence of SEQ ID NO:1 is a much more potent cancer immunotherapeutic for HPV immortalized tumors than an isogenic strain of *vaccinia* that carries the gene for E7 protein alone. In comparison, a short fusion protein Lm-AZ/-E7 comprising the E7 antigen fused to the promoter, signal sequence and the first 7 amino acid residues of LLO was an ineffective anti-tumor immunotherapeutic. This short fusion protein terminates directly before the PEST-like sequence and does not contain it. In a first set of experiments, the HPV-E7 antigen was expressed in *L. monocytogenes*. An *L. monocytogenes* recombinant that expressed E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The scheme for this is depicted in FIG. 1. The advantage in using this type of transformation is that resulting recombinants are stably transformed and contain no drug selection markers since the CAT gene, included in the plasmid to select for successful transformants after electroporation, is excised during a second recombination event. The expression and secretion of the antigen from the resulting recombinants, Lm-E7, was verified by Western Blot. In addition, therapeutic effects of Lm-E7 were optimized. For example, it was found that the best results were achieved delivering the vaccine orally as compared to parenterally and in a combined protection and regression mode that requires priming with Lm-E7 before tumor challenge and then administering Lm-E7 therapeutically after tumor challenge. Table 1 provides more details for optimized anti-tumor effects observed in this model in three different tumor cell lines, TC-1, C3 and EL-4/E7. Bacteria were delivered orally 14 and 7 days prior to tumor challenge and days 7 and 14 following tumor challenge. Delivery of $10^6$ bacteria intraperitoneally in a similar protocol provided no long-term protection. However, better protection was observed when Lm-E7 was delivered orally. More specifically, with this regimen approximately 50% of the animals remained tumor free in perpetuity and immunization seriously retarded tumor growth in all animals.

TABLE 1

Treatment with Lm-E7

| | Number of tumor free animals versus total in study (number survived) | | |
|---|---|---|---|
| Treatment | $10^5$ TC-1 on day 60 | $10^6$ C3 on day 42 | $5 \times 10^5$ EL-4/E7 on day 40 |
| $10^8$ Lm-E7 | 3/8(5) | 4/8(8) | 4/8(6) |
| $10^8$ Lm-Gag(ZY-18) | 2/8(2) | 0/8(0) | 2/8(0) |
| Naive | 0/8(0) | 0/8(0) | 1/8(0) |

Animals administered TC-1 or EL-4/E7 tumor cells that were tumor free were re-challenged on day 60 with TC-1 or day 40 EL-4/E7, respectively. The two animals in each group that had been immunized with Lm-Gag grew tumors whereas the animals immunized with Lm-E7 remained tumor free until termination of the experiment (day 124 in the case of TC-1 and day 54 for EL-4/E7).

Compared to results previously disclosed with Lm-NP and the RENCA, CT-26 and B16F10-NP models (Pan et al. 1995), the Lm-E7 was less effective than expected. Accordingly, an Lm-E7 construct was prepared in accordance with the method taught for preparation of the Lm-NP construct of Pan et al. (*Cancer Res.* 1995 55:4776-4779).

Figure 2:
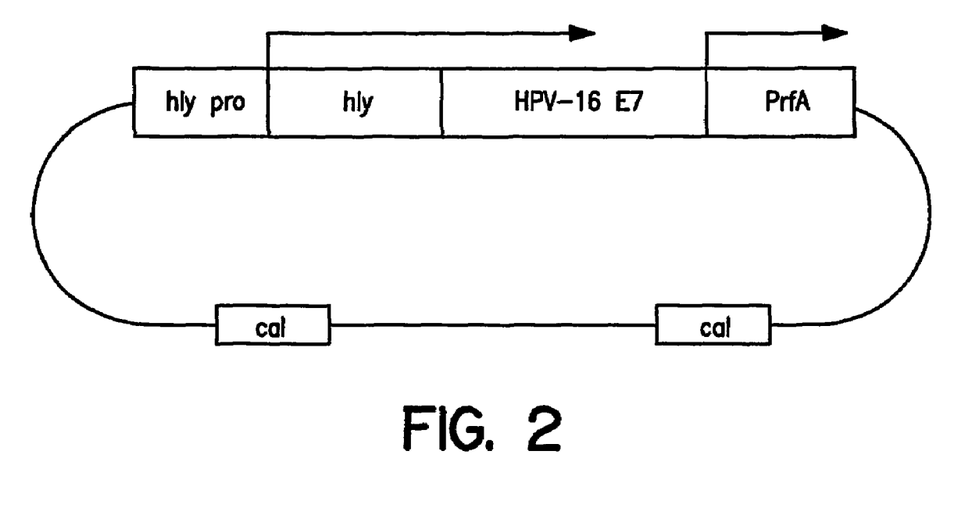
FIG. 2 is a diagram of a preferred multi-copy plasmid containing prfA and E7 fused to a truncated form of the hly gene (Δhly) that produced ΔLLO.

Specifically, a second *L. monocytogenes* vaccine that expresses a E7 fusion protein, referred to as Lm-LLO-E7, was prepared by complementing a prfA-deletion mutant with a plasmid containing a copy of the prfA gene and a copy of the E7 gene fused to a form of the hly gene truncated to eliminate the hemolytic activity of the enzyme, ΔLLO (see FIG. 2). Functional LLO is maintained by the organism via the endogenous chromosomal copy of hly. The expression and secretion of the fusion protein was verified by Western blot.

The ability of the Lm-LLO-E7 and Lm-E7 vaccine to induce anti-tumor immunity was then compared in a regression model. As shown in Table 2, Lm-LLO-E7 was found to be more effective than Lm-E7. This difference in efficacy is believed to be due to the presence of the PEST-like sequence, SEQ ID NO:1, in Lm-LLO-E7.

TABLE 2

Number of mice cured of TC-1 tumor at conclusion of experiment

| Treatment | Mice TC-1 free at day 45 | Mice alive at day 45 | Mice alive at day 134 |
| --- | --- | --- | --- |
| Naive | 0/8 | 0/8 | 0/8 |
| Lm-LLO-E7 | 4/8 | 8/8 | 4/8 |
| Lm-E7 | 0/8 | 7/8 | 0/8 |

Thus, expression of the foreign gene as a fusion protein with ΔLLO enhances the immunogenicity of the antigen.

Additional experiments were performed to compare the ability of Lm-E7 with Lm-LLO-E7 to induce the regression of established sub-cutaneous HPV-16 immortalized tumors from C57Bl/6 mice. In these experiments, mice were immunized i.p. with 0.1 LD$_{50}$ with one of four constructs, Lm-E7, Lm-Gag (isogenic with Lm-E7 except for the antigen expressed), Lm-LLO-E7 or Lm-LLO-NP. Lm-LLO-NP is isogenic with Lm-LLO-E7 but expresses influenza antigen. A second immunization was performed on day 14. Six of eight mice immunized with Lm-LLO-E7 were cured of their tumors and remained tumor free. None of the other animals showed any regression of the established tumors. Similar results have been achieved for Lm-LLO-E7 under different immunization protocols. Further, just one immunization has been demonstrated to cure mice of established TC-1 of 5 mm diameter.

In order to confirm the generality of the finding that fusing LLO to an antigen confers enhanced immunity, a version of Lm-NP similar to Lm-E7 was constructed. This recombinant was prepared as shown in FIG. 1 except that influenza nucleoprotein replaced E7 as the antigen. The ability of the new Lm-NP was compared with Lm-LLO-NP (described in U.S. Pat. No. 5,830,702 and prepared as shown in FIG. 2). In these experiments, 32 BALB/c mice were inoculated with 5×10$^5$ RENCA-NP tumor cells. RENCA-NP is a renal cell carcinoma retrovirally transduced with influenza nucleoprotein NP (described in U.S. Pat. No. 5,830,702). After palpable macroscopic tumors had grown on day 10, eight animals in each group were immunized i.p. with 0.1LD$_{50}$ with one of three constructs, Lm-NP, Lm-Gag (isogenic with Lm-NP except for the antigen expressed) and Lm-LLO-NP. The animals received a second immunization one week later. Eight animals were left untreated. At the end of the experiment on day 40, all the mice in the naive group had large tumors or had died. Only one mouse in the group that received Lm-Gag and two mice in the group that received Lm-NP were tumor free. This experiment shows that fusing an antigen to LLO is not restricted to E7 and suggests that the form of the antigen is not important.

Additional experiments were performed to confirm the enhanced therapeutic efficacy of a fusion protein comprising the E7 antigen and a truncated form of listeriolysin O. In these experiments a *vaccinia* vector that expresses E7 as a fusion protein with a non-hemolytic truncated form of listeriolysin O was constructed. The WR strain of *vaccinia* was used as the recipient and the fusion gene was excised from the listerial plasmid and inserted into pSC11 under the control of the p75 promoter. This vector was chosen because it is the transfer vector used for the *vaccinia* constructs Vac-SigE7Lamp and Vac-E7 and would therefore allow direct comparison with Vac-LLO-E7. In this way all three *vaccinia* recombinants would be expressed under control of the same early/late compound promoter p7.5. In addition SC11 allows the selection of recombinant viral plagues to TK selection and β-galactosidase screening.

Figure 3:
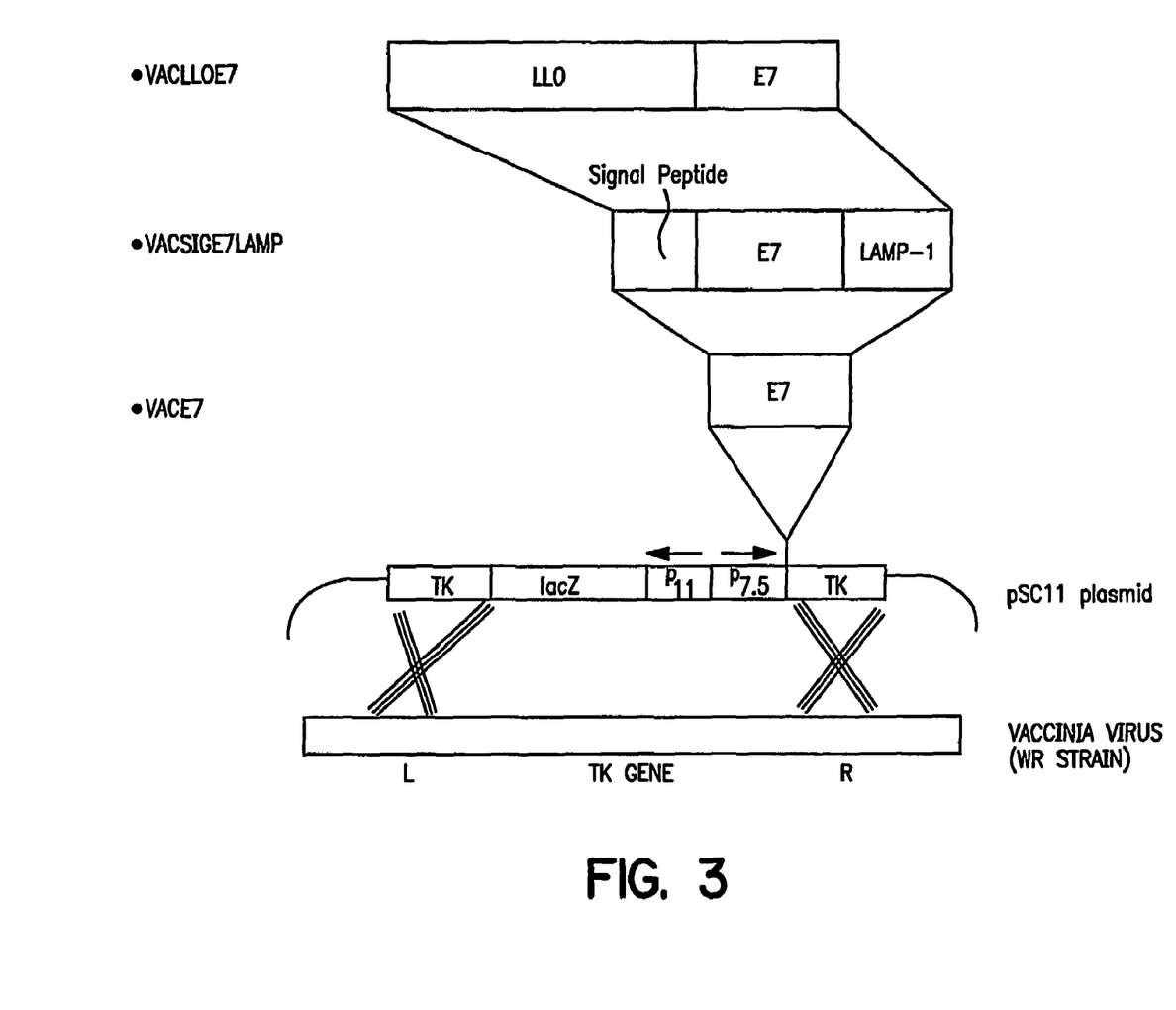
FIG. 3 is a diagram of various *Vaccinia* virus constructs expressing different forms of HPV16 E7 protein.

FIG. 3 shows the various *vaccinia* constructs used in these experiments. Vac-SigE7Lamp is a recombinant *vaccinia* virus that expressed the E7 protein fused between lysosomal associated membrane protein (LAMP-1) signal sequence and sequence from the cytoplasmic tail of LAMP-1 (Lin et al. *Proc. Natl. Acad. Sci. USA* 1995 92:11671-5; Wu et al. *Cancer Res.* 1996 56:21-6). It was designed to facilitate the targeting of the antigen to the MHC class II pathway.

The following modifications were made to allow expression of the gene product by *vaccinia:* (a) the T5XT sequence that prevents early transcription by *vaccinia* was removed from the 5' portion of the LLO-E7 sequence by PCR; and (b) an additional XmaI restriction site was introduced by PCR to allow the final insertion of LLO-E7 into SC11. Successful introduction of these changes (without loss of the original sequence that encodes for LLO-E7) was verified by sequencing. The resultant pSC11-E7 construct was used to transfect the TK-ve cell line CV1 that had been infected with the wildtype *vaccinia* strain, WR. Cell lysates obtained from this co-infection/transfection step contain *vaccinia* recombinants that were plaque purified 3 times. Expression of the LLO-E7 fusion product by plaque purified *vaccinia* was verified by Western blot using an antibody directed against the LLO protein sequence. In addition, the ability of Vac-LLO-E7 to produce CD8+ T cells specific to LLO and E7 was determined using the LLO(91-99) and E7(49-57) epitopes of Balb/c and C57/BL6 mice, respectively. Results were confirmed in a chromium release assay.

Tumor rejection studies were performed with TC-1 following the same protocol as described supra. Two experiments were performed with differing delays before treatment was started. In one experiment, treatments were initiated when the tumors were about 3 mm in diameter. As of day 76, 50% of the Vac-LLO-E7 treated mice are tumor free and 25% of the Vac-SigE7Lamp mice are tumor free.

In the second experiment, TC-1 tumors were grown to a larger size (5 to 6 mm). The LLO-E7 fusion protein based vectors were then compared against a larger number of vectors. Although some of the vaccine groups showed significant temporary regression of TC-1, by day 65 the data clearly shows that Lm-LLO-E7 and Vac-LLO-E7 are the most effective vaccines with respect to the ability to permanently induce the regression of established TC-1. Only 12% of the Vac-SigE7Lamp treated mice were tumor free while 37% of the Vac-LLO-E7 and Lm-LLO-E7 mice were tumor free. All other mice were dead.

Thus, expression of the antigen as a fusion protein with a non-hemolytic truncated form of listeriolysin O in host cell systems in *listeria* and host cell systems other than *Listeria* results in enhanced immunogenicity of the antigen. While comparative experiments were performed with *vaccinia*, a multitude of other plasmids and expression systems which can be used to express these fusion proteins are known. For example, bacterial vectors useful in the present invention include, but are not limited to *Salmonella* sp., *Shigela* sp., BCG, *L. monocytogenes* and *S. gordonii*. In addition the fusion proteins can be delivered by recombinant bacterial vectors modified to escape phagolysosomal fusion and live in the cytoplasm of the cell. Viral vectors useful in the present invention include, but are not limited to, *Vaccinia*, Avipox, Adenovirus, AAV, *Vaccinia* virus NYVAC, Modified *vaccinia* strain Ankara (MVA), Semliki Forest virus, Venezuelan equine encephalitis virus, herpes viruses, and retroviruses. Naked DNA vectors can also be used.

Accordingly, the present invention provides methods for enhancing the immunogenicity of an antigen via fusion of the antigen to a non-hemolytic truncated form of listeriolysin O or ΔLLO. In a preferred embodiment, the antigen is fused to the PEST-like amino acid sequence, SEQ ID NO:1, of LLO.

The present invention also provides methods for enhancing cell mediated and anti-tumor immunity and compositions with enhanced immunogenicity which comprise a PEST-like amino acid sequence derived from a prokaryotic organism fused to or embedded within an antigen. The PEST-like sequence can be fused to either the amino terminus or the carboxy terminus of the antigen. As demonstrated herein, fusion of an antigen to the PEST-like sequence of *L. monocytogenes* enhanced cell mediated and anti-tumor immunity of the antigen. It is believed that fusion of an antigen to other PEST-like sequences derived from other prokaryotic organisms will also enhance immunogenicity of the antigen. PEST-like sequence of other prokaryotic organism can be identified routinely in accordance with methods such as described by Rechsteiner and Roberts (TBS 21:267-271,1996) for *L. monocytogenes*. Alternatively, PEST-like amino acid sequences from other prokaryotic organisms can also be identified based by this method. Other prokaryotic organisms wherein PEST-like amino acid sequences would be expected to include, but are not limited to, other *Listeria* species. For example, the *L. monocytogenes* protein ActA contains four such sequences. These are KTEEQPSEVNTGPR (SEQ ID NO:2), KASVTDTSEGDLDSSMQSADESTPQPLK (SEQ ID NO:3), KNEEVNASDFPPPPTDEELR (SEQ ID NO:4), and RGGIPTSEEFSSLNSGDFTDDENSETTEEEIDR (SEQ ID NO:5). Also Streptolysin O from *Streptococcus* sp. contain a PEST-LIKE sequence. For example, *Streptococcus pyogenes* Streptolysin O comprises the PEST-like sequence KQNTASTETTTTNEQPK (SEQ ID NO:6) at amino acids 35-51 and *Streptococcus equisimilis* Streptolysin O comprises the PEST-like sequence KQNTANTETTTTNEQPK (SEQ ID NO:7) at amino acids 38-54. Further, it is believed that the PEST-like sequence can be embedded within the antigenic protein. Thus, for purposes of the present invention, by "fusion" it is meant that the antigenic protein comprises both the antigen and the PEST-like amino acid sequence either linked at one end of the antigen or embedded within the antigen.

In a preferred embodiment, fusion proteins of the present invention are produced recombinantly via a plasmid which encodes either a truncated form of the listeriolysin O comprising the PEST-like amino acid sequence of *L. monocytogenes* or a PEST-like amino acid sequence derived from another prokaryotic organism and the antigen. However, the antigen may also be chemically conjugated to the truncated form of listeriolysin O comprising the PEST-like amino acid sequence of *L. monocytogenes* or a PEST-like amino acid sequence derived from another prokaryotic organism. For purposes of the present invention, by "antigen" it is meant to include the native antigen gene or gene product or truncated versions of these that include identified T cell epitopes. These fusion proteins can then be incorporated into vaccines for administration to animals, preferably humans, to invoke an enhanced immune response against the antigen of the fusion protein. In one embodiment, the fusion proteins of the present invention are delivered as DNA vaccines, RNA vaccines or replicating RNA vaccines. As will be obvious to those of skill in the art upon this disclosure, vaccines comprising the fusion proteins of the present invention are particularly useful in the prevention and treatment of infectious and neoplastic diseases.

These vaccines may further comprise adjuvants. Examples of adjuvants useful in these vaccines include, but are not limited to, unmethylated CpG, quill glycosides, CFA, QS21, monophosphoryl lipid A, liposomes, and bacterial mitogens and toxins.

The following examples are provided for illustrative purposes only and are not intended to limit the invention.

EXAMPLES

Example 1

Tumor Cell Lines

TC-1 is a lung epithelial cell from C57BL/6 mice immortalized by HPV-16 E6 and E7 and transformed by pVEJB expressing activated human c-HA-ras. C3 is a mouse embryo cell frp, C57BL/6 mice immortalized with the complete genome of HPV16 and transformed with pEJ-ras. EL-4/E7 is the thymoma EL-4 retrovirally transduced with E7.

Example 2

Comparison of Efficacy of Lm-GG/E7, Lm-AZ/E7 and Vac-SigE7Lamp

TC-1 ($1\times10^5$) or C-3 ($5\times10^5$) tumor cells were implanted subcutaneously in mice and allowed to grow for 7 to 9 days by which time they were palpable (~5 mm in size). Mice were then immunized i.p. with one of three constructs, Vac-SigE7Lamp ($10^7$ PFU), Lm-E7 ($10^6$ CFU) or Lm-LLO-E7 ($10^7$ CFU). Animals received Lm-LLO-E7 and LM-E7 on days 7 and 14. Surviving mice were re-challenged with $10^5$ TC-1 on day 43.

Example 3

Comparison of Efficacy of Vac-LLO-E7, Vac-E7 and Vac-SigE7Lamp

Four groups of 8 mice were implanted with $10^5$ cells of TC-1. After 7 days the tumors were approximately 4 mm in size. One group of mice was untreated. Each of the other groups received $10^7$ PFU of either Vac-E7, Vac-LLO-E7 or Vac-Sig-E7-lamp 7. A booster dose was administered on day 14.

Example 4

Comparison of efficacy of Vac-LLO-E7 and Lm-LLO-E7 with Various Other Vectors

TC-1 tumor cells ($2\times10^5$)were implanted s.c. on the left flank in 96 C57BL/6 mice and allowed to grow for 7 days. The mice were divided into groups of 8 mice and each group was treated with one of the following vaccine: naive (no vaccine); Vac SigE7Lamp, $10^7$ PFU, i.p.; Vac-LLO-E7, $10^7$ PFU, i.p.; or Lm-LLO-E7, $10^7$ PFU, i.p. The animals received a booster immunization one week later. Tumor growth was followed every two days by caliper measurement and recorded as the average of the narrowest and longest surface length. Immune parameters were also determined.

Example 5

Construction of Lm-LLOPEST-E7

The LLO-PEST-E7 fragment can be constructed via SOEing PCR.

In Step 1 of this method, PCR reaction 1 uses primer pair GG-36/GG-78 or GG-77/AZ-9 with pGG-55 for the template. PCR reaction 2 uses LLO-PEST and E7 products from the first reaction as templates and the primers GG-36 and AZ-9.

```
                                         (SEQ ID NO: 8)
GG-36:  5'-GCTAGCCCTCCTTTGATTAGTATATTC-3'

(SEQ ID NO: 9)
GG-77:  5'-GCGGATGAAATCGATAAGCATGGAGATACACCTACA-3'

(SEQ ID NO: 10)
GG-78:  3'-CGCCTACTTTAGCTATTCGTACCTCTATGTGGATGT-5'

(SEQ ID NO: 11)
AZ-9:   3'-GAGTCTTTGGTATTGGGCCC-5'
```

In step 2, the final SOEing PCR product of 0.7 Kb is ligated into the TA vector pCR2.1.

In step 3, the LLO-PEST-E7 is digested from the plasmid with the enzyme NheI for 2 hours followed by ethanol precipitation and the enzyme XmaI overnight. The prfA fragment from pGG-49 is digested with the enzyme SalI for 2 hours followed by ethanol precipitation and XmaI overnight. pDP-2028 is digested with SalI and XbaI for 2 hours followed by ethanol precipitation and resuspension in Tris:EDTA (TE). The fragment can be stored overnight at 4° C.

In step 4, the 0.7 Kb LLO-PEST-E7, 1.0 Kb prfA and the 9.7 Kb plasmid are ligated. This plasmid is then used to transform XFL-7. Secretion of a 15 Kb fragment can be verified via Western blot. Efficacy is verified against TC-1 tumors.

Alternatively, a chromosomal integrant can be generated by amplifying the LLO-PEST-E7 fragment using the primer AZ-B (5'-GCTCTAGATTATGGTTTCTGAG-3'; SEQ ID NO:12) to install a 3' XbaI site and primer ZY-3 (5'-GGGG-TACCCTCCTTTGATTAGTATAT-3'; SEQ ID NO:13) to install a 5' KpnI site. pZY-37 and the LLO-PEST-E7 fragment are digested with KpnI and XbaI separately or in NEB buffer 2+ BSA overnight. The fragment is ligated into pZY-37 and the following protocol for chromosomal integration is followed. Secretion and efficacy are verified as described above.

---

What is claimed is:

1. A composition with enhanced cell-mediated immunity and anti-tumor immunity comprising a fusion protein consisting of a PEST-like amino acid sequence selected from the group consisting of SEQ ID NOs: 1-7 fused to or embedded within an antigen.

2. The composition of claim 1, wherein said PEST-like amino acid sequence consists of SEQ ID No: 1.

3. The composition of claim 1, further comprising an adjuvant.

4. A method of retarding tumor growth in a subject, comprising administering to said subject a composition comprising a fusion protein consisting of a PEST-like amino acid sequence selected from the group consisting of SEQ ID NOs: 1-7 fused to or embedded within an antigen associated with said tumor.

5. The method of claim 4, therein said PEST-like amino acid sequence is from a listeriolysin (LLO) protein.

6. The method of claim 4, wherein said PEST-like amino acid sequence is from an ActA protein.

7. The method of claim 4, wherein said PEST-like amino acid sequence is from a Streptolysin protein.

8. The method of claim 4, wherein said PEST-like amino acid sequence consists of SEQ ID No: 1.

9. The method of claim 4, wherein said PEST-like amino acid sequence is selected from the group consisting of SEQ ID Nos: 2-5.

10. The method of claim 4, wherein said PEST-like amino acid sequence is selected from the group consisting of SEQ ID Nos: 6-7.

11. A method of inducing the regression of a tumor in a subject, comprising administering to said subject a composition comprising a fusion protein consisting of a PEST-like amino acid sequence selected from the group consisting of SEQ ID NOs: 1-7 fused to or embedded within an antigen associated with said tumor.

12. The method of claim 11, wherein said PEST-like amino acid sequence is from a listeriolysin (LLO) protein.

13. The method of claim 11, wherein said PEST-like amino acid sequence is from an ActA protein.

14. The method of claim 11, wherein said PEST-like amino acid sequence is from a Streptolysin protein.

15. The method of claim 11, wherein said PEST-like amino acid sequence consists of SEQ ID No: 1.

16. The method of claim 11, wherein said PEST-like amino acid sequence is selected from the group consisting of SEQ ID Nos: 2-5.

17. The method of claim 11, wherein said PEST-like amino acid sequence is selected from the group consisting of SEQ ID Nos: 6-7.

18. The composition of claim 1, wherein said PEST-like amino acid sequence is from an ActA protein.

19. The composition of claim 1, wherein said PEST-like amino acid sequence is selected from the group consisting of SEQ ID Nos: 2-5.

20. The composition of claim 1, wherein said PEST-like amino acid sequence is selected from the group consisting of SEQ ID Nos: 6-7.

21. A method for enhancing the cell-mediated immunity of an antigen in a subject, comprising administering to said subject a composition comprising a fusion protein consisting of a PEST-like amino acid sequence selected from the group consisting of SEQ ID NOs: 1-7 fused to or embedded within said antigen.

22. The method of claim 21, wherein said PEST-like amino acid sequence is from a listeriolysin (LLO) protein.

23. The method of claim 21, wherein said PEST-like amino acid sequence is from an ActA protein.

24. The method of claim 21, herein said PEST-like amino acid sequence is from a Streptolysin protein.

25. The method of claim 21, wherein said PEST-like amino acid sequence consists of SEQ ID No: 1.

26. The method of claim 21, wherein said PEST-like amino acid sequence is selected from the group consisting of SEQ ID Nos: 2-5.

27. The method of claim 21, wherein said PEST-like amino acid sequence is selected from the group consisting of SEQ ID Nos: 6-7.

28. A method for invoking an enhanced cell-mediated or anti-tumor immunogenic response to an antigen in a subject, comprising administering to said subject a composition comprising a fusion protein consisting of a PEST-like amino acid sequence selected from the group consisting of SEQ ID NOs: 1-7 fused to or embedded within said antigen.

29. The method of claim 28, wherein said PEST-like amino acid sequence is from a listeriolysin (LLO) protein.

30. The method of claim 28, wherein said PEST-like amino acid sequence is from an ActA protein.

31. The method of claim 28, wherein said PEST-like amino acid sequence is from a Streptolysin protein.

32. The method of claim 28, wherein said PEST-like amino acid sequence consists of SEQ ID No: 1.

33. The method of claim 28, wherein said PEST-like amino acid sequence is selected from the group consisting of SEQ ID Nos: 2-5.

34. The method of claim 28, wherein said PEST-like amino acid sequence is selected from the group consisting of SEQ ID Nos: 6-7.

35. The composition of claim 1, wherein said PEST-like amino acid sequence is from a listeriolysin (LLO) protein.

* * * * *